(12) United States Patent
Martel

(10) Patent No.: US 10,952,803 B2
(45) Date of Patent: Mar. 23, 2021

(54) METHODS AND APPARATUS FOR DIPOLE FIELD NAVIGATION FOR DIRECT TARGETING OF THERAPEUTIC AGENTS

(71) Applicant: POLYVALOR, LIMITED PARTNERSHIP, Montreal (CA)

(72) Inventor: Sylvain Martel, Quebec (CA)

(73) Assignee: POLYVALOR, LIMITED PARTNERSHIP, Montréal (CA)

( * ) Notice: Subject to any disclaimer, the term of this patent is extended or adjusted under 35 U.S.C. 154(b) by 663 days.

(21) Appl. No.: 15/118,354

(22) PCT Filed: Feb. 16, 2015

(86) PCT No.: PCT/CA2015/050110
§ 371 (c)(1),
(2) Date: Aug. 11, 2016

(87) PCT Pub. No.: WO2015/120556
PCT Pub. Date: Aug. 20, 2015

(65) Prior Publication Data
US 2017/0165020 A1 Jun. 15, 2017

Related U.S. Application Data

(60) Provisional application No. 61/940,051, filed on Feb. 14, 2014.

(51) Int. Cl.
*A61B 34/00* (2016.01)
*A61B 5/055* (2006.01)
(Continued)

(52) U.S. Cl.
CPC .............. *A61B 34/73* (2016.02); *A61B 5/055* (2013.01); *A61B 5/4839* (2013.01);
(Continued)

(58) Field of Classification Search
CPC .................. A61B 34/73; A61B 5/4839; A61B 2017/00876; A61B 2018/00404;
(Continued)

(56) References Cited

U.S. PATENT DOCUMENTS 6,212,419 B1 * 4/2001 Blume .................... A61B 34/73
600/407
2005/0182315 A1 * 8/2005 Ritter ................. G01R 33/3806
600/411
(Continued)

OTHER PUBLICATIONS

M.D. Tehrani, M.O. Kim, J. Yoon, "A Novel Electromagnetic Actuation System for Magnetic Nanoparticle Guidance in Blood Vessels", IEEE Trans. Magn., vol. 50, pp. 1-12 (Jul. 2014).*
(Continued)

*Primary Examiner* — Bill Thomson
*Assistant Examiner* — Aminah Asghar
(74) *Attorney, Agent, or Firm* — Anglehart et al.

(57) ABSTRACT

A method for navigating therapeutic, diagnostic or imaging agents in a vascular network or body cavity is introduced. The method is characterized by high directional gradients and a high magnetic field strength. The latter is used to saturate the magnetization of magnetic therapeutic agents such that when combined with high directional gradients, improved navigation of the magnetic therapeutic agents can be provided at various depths within a patient's body.

20 Claims, 21 Drawing Sheets

(51) Int. Cl.
| | |
|---|---|
| A61B 5/00 | (2006.01) |
| A61B 6/00 | (2006.01) |
| A61B 8/08 | (2006.01) |
| A61K 49/18 | (2006.01) |
| A61K 41/00 | (2020.01) |
| A61M 31/00 | (2006.01) |
| A61N 2/00 | (2006.01) |
| G01R 33/38 | (2006.01) |

(52) U.S. Cl.
CPC ............ *A61B 6/4258* (2013.01); *A61B 6/504* (2013.01); *A61B 8/0891* (2013.01); *A61K 41/00* (2013.01); *A61K 49/1827* (2013.01); *A61M 31/005* (2013.01); *A61N 2/004* (2013.01); *G01R 33/38* (2013.01); *A61B 2034/732* (2016.02); *A61B 2560/063* (2013.01)

(58) Field of Classification Search
CPC .... A61B 17/22012; A61B 5/055–0555; A61B 2034/731–733; A61K 49/1827; A61K 41/00; A61K 9/0009; A61K 49/18; G01R 33/5601; G01R 33/285; G01R 33/20–64; A61M 2037/0007; H01F 7/0226; H01F 7/0284

See application file for complete search history.

(56) References Cited

U.S. PATENT DOCUMENTS

| | | | | |
|---|---|---|---|---|
| 2007/0231393 | A1* | 10/2007 | Ritter | A61K 9/0009 424/489 |
| 2008/0275336 | A1* | 11/2008 | Deschamps | A61B 6/032 600/425 |
| 2009/0062646 | A1* | 3/2009 | Creighton, IV | A61B 5/062 600/437 |
| 2013/0046169 | A1* | 2/2013 | Weinberg | A61N 2/02 600/411 |
| 2015/0057676 | A1* | 2/2015 | Muntwyler | A61B 17/00234 606/130 |
| 2016/0144200 | A1* | 5/2016 | Leach | A61N 5/1039 600/411 |

OTHER PUBLICATIONS

Manasmita Das et al.,"Bio-functionalization of magnetite nanoparticles using an aminophosphonic acid coupling agent: new, ultradispersed, iron-oxide folate nanoconjugates for cancer-specific targeting", 2008 Nanotechnology 19 415101.*

Manasmita Das et al.,"Bio-functionalization of magnetite nanoparticles using an aminophosphonic acid coupling agent: new, ultradispersed, iron-oxide folate nanoconjugates for cancer-specific targeting", 2008 Nanotechnology 19 415101 (Year: 2008).*

A. Amirfazli in "Magnetic Nanoparticles Hit the Target", Nat. Nanotechnol., vol. 2, No. August, pp. 467-468, 2007, Abstract.

A. Senyei, K. Widder and G. Czerlinski in "Magnetic Guidance of Drug Carrying Microspheres", J. Appl. Phys., vol. 49, No. 6, p. 3578, 1978, Abstract.

C. Sun, J. S. H. Lee, and M. Zhang in "Magnetic Nanoparticles in MR Imaging and Drug Delivery", pp. 1252-1265, 2008.

C. Tremblay, B. Conan, D. Loghin, A. Bigot and S. Manel in "Fringe Field Navigation for Catheterization" in 6th Eur. Conf. Int. Fed. Med. Biol. Eng., 2014, pp. 379-382.

H. Choi et al, EMA System with Gradient and Uniform Saddle Coils for 3D Locomotion of Microrobot, Sensors Actuators A Phys., vol. 163, No. 1, pp. 410-417, Sep. 2010.

H. Keller, A. Juloski, H. Kawano, M. Bechtold, A. Kimura, H. Takizawa and R. Kuth, "Method for Navigation and Control of a Magnetically Guided Capsule Endoscope in the Human Stomach", in Proc. IEEE RAS EMBS Int. Conf. Biomed. Robot. Biomechatronics, 2012, pp. 859-865.

J. Johnson, T. Kent, J. Koda, C. Peterson, S. Rudge and G. Tapolsky, "The MTC Technology: A Platform Technology for the Site-Specific Delivery of Pharmaceutical Agents", Eur. Cells Mater., vol. 3, pp. 12-15, 2002.

J.-B. Mathieu and S. Martel in "Steering of Aggregating Magnetic Microparticles using Propulsion Gradients Coils in an MRI Scanner", Magn. Reson. Med., vol. 63, No. 5, pp. 1336-1345, 2010.

J.-B. Mathieu, G. Beaudoin, and S. Martel, "Method of Propulsion of a Ferromagnetic Core in the Cardiovascular System through Magnetic Gradients Generated by an MRI System", IEEE Trans. Biomed. Eng., vol. 53, No. 2, pp. 292-299, 2006.

K. J. Widder, R. M. Morrist, G. Pooret, D. P. Howard, and A. E. Senyeit in "Tumor Remission in Yoshida Sarcoma-Bearing Rats by Selective Targeting of Magnetic Albumin Microspheres Containing Doxorubicin", in Proc. Natl. Acad. Sci. U. S. A., vol. 78, No. 1, 1981, pp. 579-581.

K. Mosbach and U. Schroder in "Preparation and Application of Magnetic Polymers for Targeting of Drugs", FEBS Lett., vol. 102, No. 1, pp. 112-116, 1979.

M. D. Tehrani, M. O. Kim and J. Yoon in "A Novel Electromagnetic Actuation System for Magnetic Nanoparticle Guidance in Blood Vessels", IEEE Trans. Magn., vol. 50, pp. 1-12, 2014.

M. P. Kummer, J. J. Abbott, B. E. Kratochvil, R. Borer, A. Sengul and B. J. Nelson, "Octomag: An Electromagnetic System for 5-DOF Wireless Micromanipulation", IEEE Trans. Robot., vol. 26, pp. 1006-1017, 2010.

Maxime Latulippe ; Sylvain Martel; Dipole Field Navigation for targeted drug delivery, IEEE RAS & EMBS 5th International Conference on Biomedical Robotics and Biomechatronics, at Sao Paulo, Brazil Aug. 2014.

N. Bertrand, J. Wu, X. Xu, N. Kamaly and O. C. Farokhzad, "Cancer Nanotechnology: The Impact of Passive and Active Targeting in the Era of Modern Cancer Biology", Adv. Drug Deliv. Rev., vol. 66, pp. 2-25, 2014.

O. Felfoul, J.-B. Mathieu, G. Beaudoin, and S. Martel "In vivo MR Tracking Based on Magnetic Signature Selective Excitation", IEEE Trans. Med. Imaging, vol. 27, pp. 28-35, 2008.

PCT/CA2015/050110 IPRP.

PCT/CA2015/050110 ISR with claims.

PCT/CA2015/050110 Search strategy.

S. D. Steichen, M. Caldorera-Moore and N. a. Peppas, "A Review of Current Nanoparticle and Targeting Moieties for the Delivery of Cancer Therapeutics", Eur. J. Pharm. Sci., vol. 48, No. 3, pp. 416-427, Feb. 2013.

S. Jeong, H. Choi, J. Choi, C. Yu, J.-o. oh Park and S. Park in "Novel Electromagnetic Actuation (EMA) Method for 3-Dimensional Locomotion of Intravascular Microrobot", Sensors Actuators A Phys., vol. 157, No. 1, pp. 118-125, Jan. 2010.

S. Martel, "Magnetic Therapeutic Delivery Using Navigable Agents", J. of Therapeutic Delivery, vol. 5, No. 2, pp. 189-204, 2014, Abstract.

S. Martel, J.-B. Mathieu, O. Felfoul, A. Chanu, E. Aboussouan, S. Tamaz, P. Pouponneau, L. Yahia, G. Beaudoin, G. Soulez, and M. Mankiewicz, "Automatic Navigation of an Untethered Device in the Artery of a Living Animal using a Conventional Clinical Magnetic Resonance Imaging System", Appl. Phys. Lett. vol. 90 No. 11 2007.

S. Tognarelli, V. Castelli, G. Ciuti, C. Natali, E. Sinibaldi, P. Dario and A. Menciassi in "Magnetic Propulsion and Ultrasound Tracking of Endovascular Devices", J. Robot. Surg., vol. 6, No. 1, pp. 5-12, 2011.

Sylvain Martel, Magnetic Navigation Control of Microagents in the Vascular Network, IEEE Control Systems vol. 33, Issue: 6, Dec. 2013.

* cited by examiner

Algorithm 1 DFNALTERNATINGOPTIM

Inputs: $node, \{\mathcal{T}_1, \mathcal{T}_2, ..., \mathcal{T}_j\}, maxIter, \varepsilon_{tol}, \delta_{min}$ $parent \leftarrow$ the parent node of $node$
for $k = 1$ to $j$ do      ▷ Get previously obtained gradients
    $G'_{prev,k} \leftarrow \text{TOTALGRADIENTAT}(parent.cores, \mathcal{T}_k.p)$
end for
$n \leftarrow 0$
while $n < maxIter$ do
    for $k = 1$ to $j$ do
        $G'_k \leftarrow \text{TOTALGRADIENTAT}(node.cores, \mathcal{T}_k.p)$
        $\xi_k \leftarrow \text{ANGLEBETWEENVECTORS}(G'_k, \mathcal{T}_k.G)$
        $\delta_k \leftarrow \text{ANGLEBETWEENVECTORS}(G'_k, G'_{prev,k})$
    end for
    $m \leftarrow \underset{m}{\text{argmax}}\,(\xi_m)$ subject to $\delta_m \geq \delta_{min}$
    if $\xi_m < \varepsilon_{tol}$ then
        break    ▷ Done optimizing this core configuration
    else
        $\mathcal{C} \leftarrow$ core associated with $\mathcal{T}_m$
        $\text{OPTIMIZE}(\mathcal{C}, \{\mathcal{T}_1, \mathcal{T}_2, ..., \mathcal{T}_K\})$     // Eqs. (30) to (33)
        for $k = 1$ to $j$ do
            $G'_{prev,k} \leftarrow G'_k$
        end for
    end if
    $n \leftarrow n + 1$
end while

FIGURE 9

Algorithm 2 DFNCHILDNODES

Inputs: $node$, $coreProtoypes$
Output: $children$ $T \leftarrow$ next target gradient in $node.tgList$
   $G' \leftarrow$ TOTALGRADIENTAT($node.cores$, $T.p$)
   $G_{add} \leftarrow T.G - G'$    ▷ additional gradient needed at $T.p$
   $children \leftarrow$ empty
   for all $C_P$ in $coreProtoypes$ do
      $d_1, d_2, d_3 \leftarrow$ COREPOS($C_P$, $G_{add}$, $T.p$)     // Eq. (29)
      for $i = 1$ to $3$ do
         $C \leftarrow$ copy of $C_P$ at position $d_i$
         Associate $C$ with $T$
         $child \leftarrow$ copy of $node$
         $child.cores$.ADD($C$)
         $child.tgList$.REMOVE($T$)
         $children$.ADD($child$)
      end for
   end for
   return $children$

FIGURE 10

Algorithm 3 DFNPROCESSNODE

Inputs: $node$, $\{T_1, T_2, ..., T_K\}$, ...?

$C \leftarrow$ the lastly added core in $node.cores$
    $T \leftarrow$ the target gradient associated with $C$
    $b \leftarrow$ CHECKPHYSCONSTR($node.cores$, $\{T_1, T_2, ..., T_K\}$)
    if $b =$ False then
        OPTIMIZE($C$, $T$)     // Eqs. (30) to (33)
    end if
    $j \leftarrow$ index of $T$
    DFNALTERNATINGOPTIM($node.cores$, $\{T_1, T_2, ..., T_j\}$)
    $b \leftarrow$ ISCONFIGVALID($node.cores$, $\{T_1, T_2, ..., T_K\}$)
    if $b =$ True then
        if $j = K$ then     ▷ All target gradients are met
            Label $node$ as Solution
        else
            $node.children \leftarrow$ DFNCHILDNODES($node$)
        end if
    else
        Label $node$ as Failure
    end if

FIGURE 11

| Bifurcation | Target gradient[a,b] | | | Associated core[c] | | Resulting gradient[b] | |
|---|---|---|---|---|---|---|---|
| | p | G | $\xi_{max}$ | R | d | G' | $\xi$ |
| 1 | (0, 0, 0) | (400, 0, 0) | $\pi/6$ | 1.27 | (−3.9, 2.8, −2.4) | (405, 0.10, −0.17) | 0.10 |
| 2 | (−4.2, −0.1, 2.2) | (400, $\pi/2$, $\pi/2$) | $\pi/6$ | 1.27 | (−9.5, 2.6, −2.8) | (343, 1.91, 1.50) | 0.35 |
| 3 | (−7.2, 0.9, 2.4) | (400, $\pi$, 0) | $\pi/6$ | 1.27 | (−8.0, 6.1, 3.1) | (400, 3.07, 0.41) | 0.07 |

[a] Position $(x, y, z)$ in cm. [b] Gradient $(G, \theta, \varphi)$, magnitude in mT/m and all angles in radians. [c] Radius in cm.

METHODS AND APPARATUS FOR DIPOLE FIELD NAVIGATION FOR DIRECT TARGETING OF THERAPEUTIC AGENTS

RELATED APPLICATIONS

This patent application is a non-provisional of and claims priority from U.S. Provisional Patent application No. 61/940,051 filed Feb. 14, 2014 entitled "Dipole Field Navigation for Targeted Drug Delivery", which is incorporated herein by reference.

TECHNICAL FIELD

This invention relates to direct targeting of therapeutic agents, and in particular to systems and methods for magnetic dipole field navigation of magnetic therapeutic agents.

BACKGROUND

Magnetic navigation of untethered devices in the human body is a promising technique for the development of new targeted, more efficient and less invasive medical interventions.

In cancer therapy for instance, although most cancers are localized, modern treatments often involve the systemic administration of chemotherapeutics. The design of therapeutics with enhanced specificity to tumor cells, known as active targeting, constitutes an important research field which has seen significant developments in the last decade. Examples of such attempts include: N. Bertrand, J. Wu, X. Xu, N. Kamaly and O. C. Farokhzad, "Cancer Nanotechnology: The Impact of Passive and Active Targeting in the Era of Modern Cancer Biology", Adv. Drug Deliv. Rev., vol. 66, pp. 2-25, 2014; and S. D. Steichen, M. Caldorera-Moore and N. a. Peppas, "A Review of Current Nanoparticle and Targeting Moieties for the Delivery of Cancer Therapeutics", Eur. J. Pharm. Sci., vol. 48, no. 3, pp. 416-27, February 2013. Therapeutic agents are still injected systemically (systematically) in the vascular network to address such cancers, however even these new anticancer drugs lead to suboptimal targeting levels when they are injected systemically. This approach leads to a suboptimal amount of therapeutic agent(s) in the (cancerous) region to be treated while affecting other healthy organs and tissues. Not only does this approach generally leads to a tiny amount of chemotherapy medication reaching a localized tumor, but since these chemical therapeutic agents do not differentiate between normal and cancerous cells, severe side effects can arise due to healthy organs and tissues being subjected to the chemical effects.

As one possible solution, the controlled endovascular navigation of therapeutic agents, directly from the injection site toward the region to be treated, is expected to yield enhanced therapeutic outcomes while minimizing secondary toxicity effects. A concept of Direct Targeting (DT) has been introduced in "Magnetic Therapeutic Delivery Using Navigable Agents", S. Martel, J. of Therapeutic Delivery, vol. 5, no. 2, pp. 189-204, 2014, which is incorporated herein by reference, wherein therapeutic agents are navigated (guided) in the vascular network directly from an injection site towards the region to be treated relying on Remote Magnetic Navigation (RMN). Typically, such navigable therapeutic agents consist of Magnetic NanoParticles (MNPs) embedded, with therapeutic agent(s), in a spherical matrix.

The MNPs, are typically superparamagnetic nanoparticles which makes them highly magnetizable when subject to a magnetic field, provide a mechanism for inducing directional (pushing/pulling) forces on the therapeutic agent(s), while acting as Magnetic Resonance Imaging (MRI) contrast agents for tracking or targeting efficiency evaluation (C. Sun, J. S. H. Lee, and M. Zhang in "Magnetic Nanoparticles in MR Imaging and Drug Delivery", pp. 1252-1265, 2008; and O. Felfoul, J.-B. Mathieu, G. Beaudoin, and S. Martel "In vivo MR Tracking Based on Magnetic Signature Selective Excitation", IEEE Trans. Med. Imaging, vol. 27, pp. 28-35, 2008, which is incorporated herein by reference). The magnetization of the superparamagnetic nanoparticles increases up to a saturation magnetization value when submitted to an increasing magnetic field strength, and the magnetization is lost when the superparamagnetic particles are removed from the magnetic field. Such a magnetic property allows the use of magnetic gradients to induce directional (pushing/pulling) forces for superparamagnetic particle navigation purposes, while reducing aggregations of the therapeutic agents once the body (patient) is removed from the interventional platform.

Hence, for a given effective volume of superparamagnetic nanoparticles being embedded in each navigable therapeutic agent, both increased magnetic field strength and increased magnetic gradient(s) are desired to achieve more effective navigation and better targeting in deep tissues. Attempts have been made without satisfactory success:

The simplest form of RMN, initially introduced more than 30 years ago by A. Senyei, K. Widder and G. Czerlinski in "Magnetic Guidance of Drug Carrying Microspheres", J. Appl. Phys., vol. 49, no. 6, p. 3578, 1978; K. Mosbach and U. Schroder in "Preparation and Application of Magnetic Polymers for Targeting of Drugs", FEBS Lett., vol. 102, no. 1, pp. 112-116, 1979; and K. J. Widder, R. M. Morrist, G. Pooret, D. P. Howard, and A. E. Senyeit in "Tumor Remission in Yoshida Sarcoma-Bearing Rats by Selective Targeting of Magnetic Albumin Microspheres Containing Doxorubicin", in Proc. Natl. Acad. Sci. U.S.A., vol. 78, no. 1, 1981, pp. 579-581; and also being developed more recently J. Johnson, T. Kent, J. Koda, C. Peterson, S. Rudge and G. Tapolsky, "The MTC Technology: A Platform Technology for the Site-Specific Delivery of Pharmaceutical Agents", Eur. Cells Mater., vol. 3, pp. 12-15, 2002; A. Amirfazli in "Magnetic Nanoparticles Hit the Target", Nat. Nanotechnol., vol. 2, no. August, pp. 467-468, 2007; and S. Tognarelli, V. Castelli, G. Ciuti, C. Natali, E. Sinibaldi, P. Dario and A. Menciassi in "Magnetic Propulsion and Ultrasound Tracking of Endovascular Devices", J. Robot. Surg., vol. 6, no. 1, pp. 5-12, 2011 consists in positioning a permanent magnet next to the targeted region in order to attract the agents. This approach, however, suffers from the rapid decay of the magnetic gradient and field strengths, thus preventing the navigation of MNPs in deep tissues. Moreover, due to the slow or lack of directional changes of the gradients, the control capabilities in complex vascular networks are very limited.

Fast directional changes of the magnetic gradients are typically required for endovascular navigation of therapeutic agents. Known magnetic navigation platforms having this capability can be categorized as Electromagnetic Actuation Magnetic Navigation Systems (EMA-MNS) and Magnetic Resonance Navigation (MRN) platforms as described in "Magnetic Therapeutic Delivery Using Navigable Agents", S. Martel, J. of Therapeutic Delivery, vol. 5, no. 2, pp. 189-204, 2014, which is incorporated herein by reference. The rapid decay of the magnetic field strength of EMA-MNS leads to suboptimal directional pulling forces being induced on the therapeutic agents when operating in deeper regions of the body. MRN has been proposed wherein directional imaging gradients are superposed on the high uniform magnetic field of a clinical MRI scanner (J.-B. Mathieu, G. Beaudoin, and S. Martel, "Method of Propulsion of a Ferromagnetic Core in the Cardiovascular System through Magnetic Gradients Generated by an MRI System", IEEE Trans. Biomed. Eng., vol. 53, no. 2, pp. 292-299, 2006; and S. Martel, J.-B. Mathieu, O. Felfoul, A. Chanu, E. Aboussouan, S. Tamaz, P. Pouponneau, L. Yahia, G. Beaudoin, G. Soulez, and M. Mankiewicz, "Automatic Navigation of an Untethered Device in the Artery of a Living Animal using a Conventional Clinical Magnetic Resonance Imaging System", Appl. Phys. Lett., vol. 90, no. 11, 2007, both of which are incorporate herein by reference). While the magnetic field strength inside the tunnel of the scanner can be sufficient to achieve depth independent saturation magnetization of the nanoparticles, MRN lacks the increased gradient magnitude achievable with EMA-MNS. Additional coil inserts can provide much higher gradients as described by J.-B. Mathieu and S. Martel in "Steering of Aggregating Magnetic Microparticles using Propulsion Gradients Coils in an MRI Scanner", Magn. Reson. Med., vol. 63, no. 5, pp. 1336-45, 2010, which is incorporated herein by reference, but the smaller inner diameter of the insert(s) prevents whole body interventions to be conducted. Although whole body MRN could be performed using ultra-high gradient scanners, such platforms are much more expensive, not widely available and the operating time for MRN conducted in complex vascular networks is limited due to excessive heating of the coils caused by switching gradients.

Multicoil-based platforms, such as Electromagnetic Actuation (EMA) systems were proposed by H. Choi, K. Cha, J. Choi, S. Jeong, S. Jeon, G. Jang, J.-o. Park and S. Park in "EMA System with Gradient and Uniform Saddle Coils for 3D Locomotion of Microrobot", Sensors Actuators A Phys., vol. 163, no. 1, pp. 410-417, September 2010; S. Jeong, H. Choi, J. Choi, C. Yu, J.-o. oh Park and S. Park in "Novel Electromagnetic Actuation (EMA) Method for 3-Dimensional Locomotion of Intravascular Microrobot", Sensors Actuators A Phys., vol. 157, no. 1, pp. 118-125, January 2010; and by M. D. Tehrani, M. O. Kim and J. Yoon in "A Novel Electromagnetic Actuation System for Magnetic Nanoparticle Guidance in Blood Vessels", IEEE Trans. Magn., vol. 50, pp. 1-12, 2014; or the OctoMag: (M. P. Kummer, J. J. Abbott, B. E. Kratochvil, R. Borer, A. Sengul and B. J. Nelson, "Octomag: An Electromagnetic System for 5-DOF Wireless Micromanipulation", IEEE Trans. Robot., vol. 26, pp. 1006-1017, 2010) and MGCE (H. Keller, A. Juloski, H. Kawano, M. Bechtold, A. Kimura, H. Takizawa and R. Kuth, "Method for Navigation and Control of a Magnetically Guided Capsule Endoscope in the Human Stomach", in Proc. IEEE RAS EMBS Int. Conf. Biomed. Robot. Biomechatronics, 2012, pp. 859-865) platforms, can provide fast variations of strong gradients by controlling currents in the coils, but still lack the magnetic field strength required to operate microscale agents at deeper regions in the body.

Alternatively, Fringe Field Navigation (FFN) was proposed recently by C. Tremblay, B. Conan, D. Loghin, A. Bigot and S. Martel in "Fringe Field Navigation for Catheterization" in 6th Eur. Conf. Int. Fed. Med. Biol. Eng., 2014, pp. 379-382, which is incorporated herein by reference, where the patient is positioned within the external fringe field of an MRI scanner and robotically moved in 6-DOF to induce variations of the gradients at the intervention site. Although it benefits from very high gradients, the field strengths achieved with FFN are higher than all methods but Magnetic Resonance Navigation (MRN) as considered by J.-B. Mathieu, G. Beaudoin and S. Martel in "Method of Propulsion of a Ferromagnetic Core in the Cardiovascular System Through Magnetic Gradients Generated by an MRI System", IEEE Trans. Biomed. Eng., vol. 53, no. 2, pp. 292-299, 2006; and by S. Martel, J. B. Mathieu, O. Felfoul, A. Chanu, E. Aboussouan, S. Tamaz, P. Pouponneau, L. Yahia, G. Beaudoin, G. Soulez and M. Mankiewicz in "Automatic Navigation of an Untethered Device in the Artery of a Living Animal Using a Conventional Clinical Magnetic Resonance Imaging System", Appl. Phys. Lett., vol. 90, no. 11, 2007, both of which are incorporated herein by reference, while being limited by relatively slow directional changes of the gradients.

SUMMARY

The most effective method to date to achieve DT of therapeutic agents in the arterial network down to the arterioles is MRN, where the high uniform field generated by the superconducting magnet of an MRI scanner (1.5 T or higher) is sufficient to induce the depth-independent saturation magnetization of the MNPs, while directional imaging gradients offer fast variation capabilities. Conventional clinical MRI scanners are however typically limited to gradient magnitudes around 40 mT/m, which limits the velocity at which microscale agents can be navigated in the vascular network using MRN. This in turn extends the interventional time required to deliver a sufficient dose to the targeted area, especially when the total number of injections becomes significant. To shorten the total time for the navigation of therapeutic agents a few tens of micrometers, gradients of the order 200-400 mT/m are required as described by J.-B. Mathieu and S. Martel in "Steering of Aggregating Magnetic Microparticles Using Propulsion Gradient Coils in an MRI Scanner", Magn. Reson. Med., vol. 63, no. 5, pp. 1336-45, May 2010 and by P. Pouponneau, J.-C. Leroux, G. Soulez, L. Gaboury and S. Martel in "Coencapsulation of Magnetic Nanoparticles and Doxorubicin into Biodegradable Microcarriers for Deep Tissue Targeting by Vascular MRI Navigation", Biomaterials, vol. 32, no. 13, pp. 3481-6, 2011, both of which are incorporated herein by reference. Additional coil inserts capable of generating such gradients can be added in the tunnel of the scanner as described in "Steering of Aggregating Magnetic Microparticles Using Propulsion Gradient Coils in an MRI Scanner" (above), but the resulting smaller diameter impedes whole-body interventions. Although ultra-high gradient MRI scanners exist (J. A. McNab, B. L. Edlow, T. Witzel, S. Y. Huang, H. Bhat, K. Heberlein, T. Feiweier, K. Liu, B. Keil, J. Cohen-Adad, M. D. Tisdall, R. D. Folkerth, H. C. Kinney and L. L. Wald, "The Human Connectome Project and Beyond: Initial applications of 300 mT/m gradients", Neuroimage, vol. 80, pp. 234-245, 2013), these are much more expensive platforms and are not widely available. Furthermore, it has been found that fast-switching gradients in MRN cause excessive heating of the coils (A. Bigot, C. Tremblay, G. Soulez and S. Martel, "Temperature Response of a Magnetic Resonance Imaging Coil Insert for the Navigation of Theranostic Agents in Complex Vascular Networks", IEEE Trans. Magn., vol. 50, no. 8, pp. 1-7, August 2014, which is incorporated herein by reference) which limits the operating time for navigation in complex vascular networks, and could potentially, with further advances in coil technology capable of much higher slew rates, induce peripheral nerve stimulation.

Prior attempts have addressed the problem of parameterizing a set of magnetic sources in order to generate a given magnetic field. One possible solution when the positions of the sources are known is to build a matrix linear equation describing the system and solve it using the pseudo-inverse techniques to find the optimal solutions (M. P. Kummer, J. J. Abbott, B. E. Kratochvil, R. Borer, A. Sengul and B. J. Nelson in "OctoMag: An Electromagnetic System for 5-DOF Wireless Micromanipulation", IEEE Trans. Robot., vol. 26, pp. 1006-1017, 2010; and B. Veron, A. Hubert, J. Abadie and N. Andreff in "Geometric Analysis of the Singularities of a Magnetic Manipulation System with Several Mobile Coils", IEEE/RSJ Int. Conf. Intel. Robot. Syst., 2013, pp. 4996-5001). Although in "Geometric Analysis of the Singularities of a Magnetic Manipulation System with Several Mobile Coils", hereinabove, the electromagnetic coils used are allowed to move, the matrix equation is built once their positions are set, i.e., the coil positions and orientations are not part of the inverse problem. Other methods exist to localize and characterize dipoles from a set of measurements of the magnetic field, e.g., for the modeling of the magnetic field measured above the earth surface (X. Luo and C. Foss in "Inverse of Magnetic Dipole Field Using a Reversible Jump Markov Chain Monte Carlo", ArXiv Phys. e-prints, no. arXiv/1310.0915, 2013), for the electro- and magneto-encephalographic source localization (M. A. Jatoi, N. Kamel, A. S. Malik, I. Faye and T. Begum in "A Survey of Methods Used for Source Localization Using EEG Signals", Biomed. Signal Process. Control, vol. 11, pp. 42-52, May 2014) and for the modeling of the magnetic cleanliness of spacecraft (N. C. Kapsalis, S.-D. J. Kakarakis and C. N. Capsalis in "Prediction of Multiple Magnetic Dipole Model Parameters from Near Field Measurements Employing Stochastic Algorithms", Prog. Electromagn. Res. Lett., vol. 34, no. May, pp. 111-122, 2012). These methods however are based on the theoretical point dipole model, which may become inaccurate in DFN if magnetic interactions occur between cores.

To achieve effective navigation of microscale therapeutic agents in the vascular network, a high magnetic field strength with high directional magnetic gradients are needed. So far, the methods that have been investigated support only one of these specifications but not both. Core dimensions can be taken into account in order to consider physical constraints (e.g., cores cannot overlap or be placed inside the patient's body).

To overcome these limitations, a new method referred to herein as Dipole Field Navigation (DFN) is introduced (M. Latulippe and S. Martel, "Dipole Field Navigation for Targeted Drug Delivery", IEEE Int. Conf. Biomed. Robot. Biomechatronics, 2014, which is incorporated herein by reference). Magnetic field gradients for DFN are created by a distorted high uniform magnetic field of a clinical MRI scanner system when one or several ferromagnetic cores are placed inside the tunnel of the MRI scanner to provide high field strength to bring magnetic agents at saturation magnetization. When positioned adequately, such cores create a pattern of magnetic field gradients exceeding 300 mT/m at any depth within the human body that cause the therapeutic agents including magnetic nanoparticles (at saturation magnetization) to follow a desired (prescribed) path in the vascular network.

In accordance with a first embodiment of the proposed solution, the magnetic inverse problem for positioning a single core is considered and feasibility of such a DFN method is demonstrated for deflecting (guiding) magnetic agents in one fluid junction (bifurcation).

In accordance with a second embodiment of the proposed solution, a method for positioning multiple cores in DFN-S is provided in order to deflect (guide) therapeutic agents through consecutive junctions (bifurcations) in a vascular network. Due to the cumulative contributions of multiple cores to total gradients, and because of the possible magnetic interactions between them, an incremental positioning algorithm is proposed, wherein cores are progressively added to a core configuration until the desired resulting magnetic gradients are met.

DFN does not have many of the constraints of gradient coil-based platforms, which include potential peripheral nerve stimulations, reduced directional changes and slew rates of gradient fields, overheating of the coils and high implementation cost. To overcome such shortcomings, soft ferromagnetic cores are positioned at specific locations inside the tunnel of a clinical MRI scanner providing a high uniform field, typically up to 3 T, sufficient to bring both the cores and the magnetic nanoparticles within therapeutic agents at full saturation magnetization. Field distortions created by the ferromagnetic cores result in gradients exceeding 300 mT/m for whole body interventions. With such cores placed at specific locations, the resulting gradients would cause the magnetic therapeutic agents to follow a prescribed (desired) path in the vascular network towards the targeted region.

BRIEF DESCRIPTION OF THE DRAWINGS

The proposed solution will be better understood by way of the following detailed description of embodiments of the invention with reference to the appended drawings, in which:

FIG. 9 is a pseudo-code listing of an alternating optimization process employed in an implementation of the second embodiment of the proposed solution;

FIG. 10 is a pseudo-code listing of a core addition and removal process employed in an implementation of the second embodiment of the proposed solution;

FIG. 11 is a pseudo-code listing of a core position and characteristics optimization process employed in an implementation of the second embodiment of the proposed solution;

DETAILED DESCRIPTION

Figure 1A:
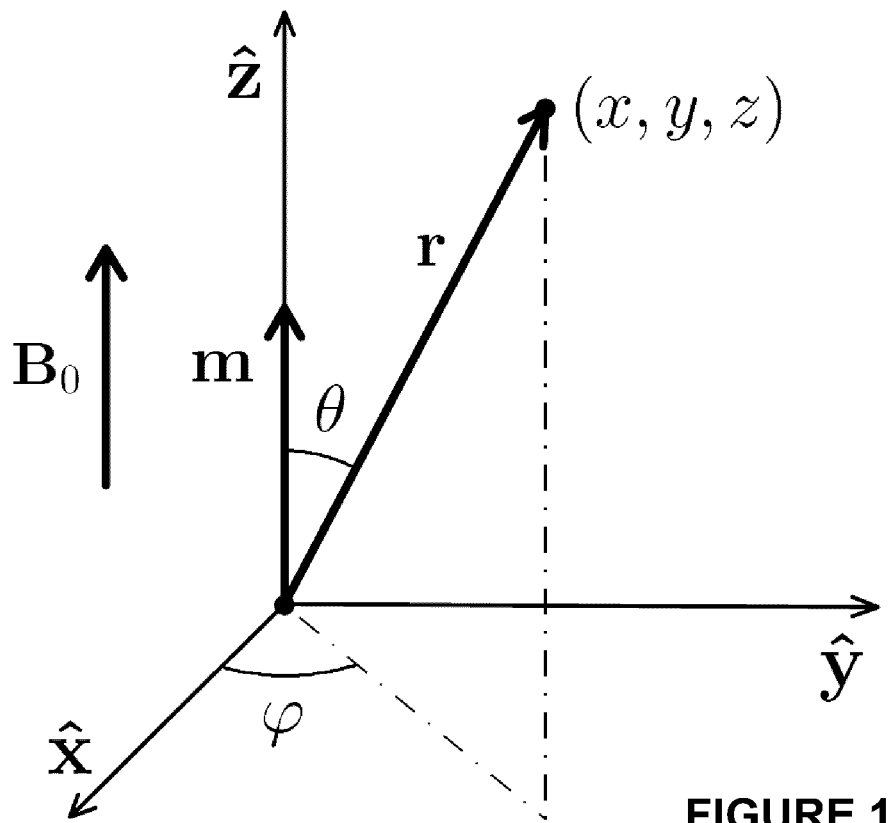
FIGS. 1A and 1B are schematic diagrams showing convention of symbols used respectively for a single core embodiment and a multicore embodiment of the proposed solution.

Some theoretical aspects of DFN are presented first followed by preliminary experimental results.

Theory

The magnetic field $B_0$ inside an MRI tunnel can be considered static and uniform. In presence of a static and homogeneous external magnetic field $B_0$, a spherical ferromagnetic core becomes uniformly magnetized. A soft ferromagnetic core placed in such a field induces a magnetic field $B_{core}$ (distortion) that adds to $B_0$, distorting the total resultant field in the tunnel:

$$B = B_0 + B_{core} \quad (1)$$

For a uniformly magnetized spherical bead of radius R, the induced magnetic field at any point $r=(x, y, z)$ around the bead is that of a dipole of equal magnetic moment m placed at the center of the bead:

$$B_{dip}(r > R) = \frac{\mu_0}{4\pi}\left[3\frac{(m \cdot r)r}{r^5} - \frac{m}{r^3}\right] \quad (2)$$

where $\mu_0 = 4\pi \times 10^{-7}$ H/m is the vacuum permeability and $r=|r|$. In the following, let $B_0 = B_0\hat{z}$ be aligned with the z-axis. For a sphere, the magnetic moment is then given by:

$$m = \frac{4\pi R^3}{3} M\hat{z} \quad (3)$$

where M is the volume magnetization of the ferromagnetic material, which depends on the static field density $B_0$. The vector m being parallel to $\hat{z}$, (parallel to $B_0$), Eq. (2) becomes:

$$B_{dip} = \frac{3\mu_0}{4\pi r^5}[3xz\hat{x} + 3yz\hat{y} + (3z^2 - r^2)\hat{z}] \quad (4)$$

which highlights the symmetry of B around $\hat{z}$ in our case.

The addition of the field B to the external field $B_0$ induces a distortion of $m_p$ the total magnetic field around the core. This distortion generates magnetic gradients that can be used to induce directional forces on magnetic particles circulating in the vicinity of the core. The force and torque exerted on a particle of magnetic moment placed in a magnetic field B are given by:

$$F_{mag} = (m_p \cdot \nabla)B = \nabla(m_p \cdot B) \quad (5)$$

$$\tau_{mag} = m_p \times B \quad (6)$$

In our case, magnetic nanoparticles (within therapeutic agents) are magnetized by the total field B, which implies that is aligned with B. $m_p$ Therefore, the latter equations simplify to:

$$F_{mag} = \nabla(m_p B) = m_p \nabla B \quad (7)$$

$$\tau_{mag} = 0 \quad (8)$$

Note that the magnetization of the particle contributes to the total field B, but since its radius $R_p \ll R_{core}$ is very small, we neglect this contribution as well as its effect on the magnetization of the core.

To further simplify Eq. (7), we consider the case where the particles are located "far enough" from the core so that the influence of $B_{core}$ on $m_p$ is negligible ("far enough" is defined below). Following this condition, $m_p$ is approximately parallel to $\hat{z}$, hence:

$$F_{mag} \approx m_p \nabla B_z \quad (9)$$

wherein the magnetic force induced on a magnetic nanoparticle is aligned with the gradient of the z-component of B at the particle location.

For a spherical magnetic core, calculating the derivative of $B_z$ using Eq. (4) yields:

$$G \equiv \nabla B_z = \nabla \left( B_0 + \frac{\mu_0 m}{4\pi} \frac{3z^2 - r^2}{r^5} \right) \quad (10)$$

$$= \frac{3\mu_0 m}{4\pi r^7} \begin{bmatrix} x(r^2 - 5z^2) \\ y(r^2 - 5z^2) \\ z(3r^2 - 5z^2) \end{bmatrix}^T \quad (11)$$

Using the convention illustrated at FIG. 1A, substituting x=r sin θ cos φ, y=r sin θ sin φ and z=r cos θ yields:

$$G = \frac{3\mu_0 m}{4\pi r^4} \begin{bmatrix} \sin\theta\cos\varphi(1 - 5\cos^2\theta) \\ \sin\theta\sin\varphi(1 - 5\cos^2\theta) \\ \cos\theta(3 - 5\cos^2\theta) \end{bmatrix}^T \quad (12)$$

Taking advantage of the symmetry of G around $\hat{z}$, the gradient can be expressed in 2D in the xz-plane. Setting φ=0, the gradient simplifies to:

$$G = \frac{3\mu_0 m}{4\pi r^4} \begin{bmatrix} \sin\theta(1 - 5\cos^2\theta) \\ \cos\theta(3 - 5\cos^2\theta) \end{bmatrix}^T \quad (13)$$

Figure 2A:
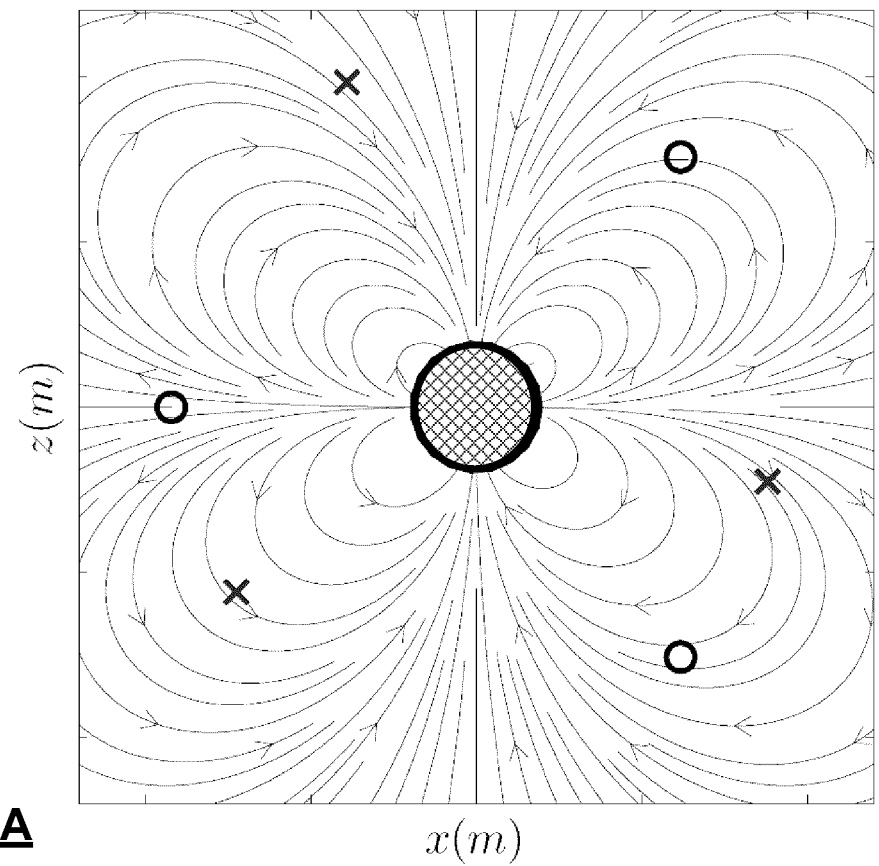
FIGS. 2A and 2B are schematic diagrams illustrating two dimensional plot of a magnetic gradient field around a magnetized spherical core illustrating respectively locations having equal magnitude and direction.

FIG. 2A illustrates the gradient field around a magnetized spherical core and depicts locations where the same gradient is obtained for two arbitrarily chosen gradients. Crosses and circles represent different locations around the core where the orientation of the gradient is $$\frac{3\pi}{4} \text{ and } -\frac{\pi}{2}$$

respectively. Note that the field line density is not proportional to the gradient magnitude.

Substituting $\nabla B_z = G$ in Eq. (9) provides an expression for the induced magnetic force between two dipoles with parallel magnetizations (i.e. a core and a particle) as a function of r, the distance between the particle to the center of the core, and θ, the angle between r and z. This result is equivalent to the one obtained by T. Fujita and M. Mamiya in "Interaction Forces Between Nonmagnetic Particles in the Magnetized Magnetic Fluid", J. Magn. Magn. Mater., vol. 65, no. 2-3, pp. 207-210, 1987. The force is purely attractive when θ=0 or θ=π and purely repulsive when θ=π/2 or θ=−π/2.

The variation of the force magnitude between two dipoles as the inverse fourth power of r was validated experimentally in the far field by R. Castañer, J. M. Medina, and M. J. Cuesta-Bolao in "The Magnetic Dipole Interaction as Measured by Spring Dynamometers", Am. J. Phys., vol. 74, no. 6, pp. 510-513, 2006; by L. E. Gayetsky and C. L. Caylor in "Measuring the Forces Between Magnetic Dipoles", Phys. Teach., vol. 45, no. 6, p. 348, 2007; and by A. Mehdizadeh, R. Mei, J. F. Klausner and N. Rahmatian in "Interaction Forces Between Soft Magnetic Particles in Uniform and Non-Uniform Magnetic Fields", Acta Mech. Sin., vol. 26, no. 6, pp. 921-929, 2010. In particular, Mehdizadeh et al. have shown this relation to be accurate when r/R>4 (for two identical soft ferromagnetic spheres). At smaller distances, the magnetization of one sphere affects the magnetization of the other and vice-versa, leading to an underestimated attractive force when θ∈{0, π} (increased magnetizations) and an overestimated repulsive force when θ∈{−π,π} (decreased magnetizations). Mehdizadeh et al. show that the change in the magnetization can be described using a simple dipole model, and thereby precisely correcting the magnetization values allows to use the same inverse 4th power law when r/R<4. Their model, however, applies only when the magnetization of the spheres lies in the linear region of the magnetization curve, which is not the case in accordance with the proposed solution. In fact, one of the advantages of working inside the tunnel of an MRI is that the core and the particles reach the saturation magnetization, maximizing the pulling (pushing) force induced on particles. The variation of the magnetization as a function of the magnetic field density B being much lower when at saturation, in accordance with the proposed solution it is reasonable to suppose herein that the dipole-dipole interaction effect is negligible at a closer distance r. Moreover, because $R_p \ll R_{core}$, it is likely that the interaction effect between the core and particles is weaker than for two identical beads. For these reasons, r/R>4 is considered herein to be a worst case limit for the validity of the above results. This constraint is conservatively used to define the "far enough" criterion introduced to obtain Eq. (9).

First Embodiment of the Proposed Solution

In accordance with a first embodiment of the proposed solution, a soft ferromagnetic core is placed inside an MRI (scanner) tunnel to distort the field $B_0$ so that the resultant magnetic gradient field makes injected particles follow a predefined path inside the vascular network. More precisely, the particles, transported by blood flow, can be deflected to veer their course in an appropriate preselected vessel branch (es) (bifurcate) towards a target region.

Such a navigation problem includes correctly positioning ferromagnetic cores such that appropriate magnetic gradients are generated at different locations inside a patient's body. In particular, gradients are needed before each vessel bifurcation (intersection) to push/pull the particles (towards) inside the desired branch.

Single Core Positioning

Figure 3:
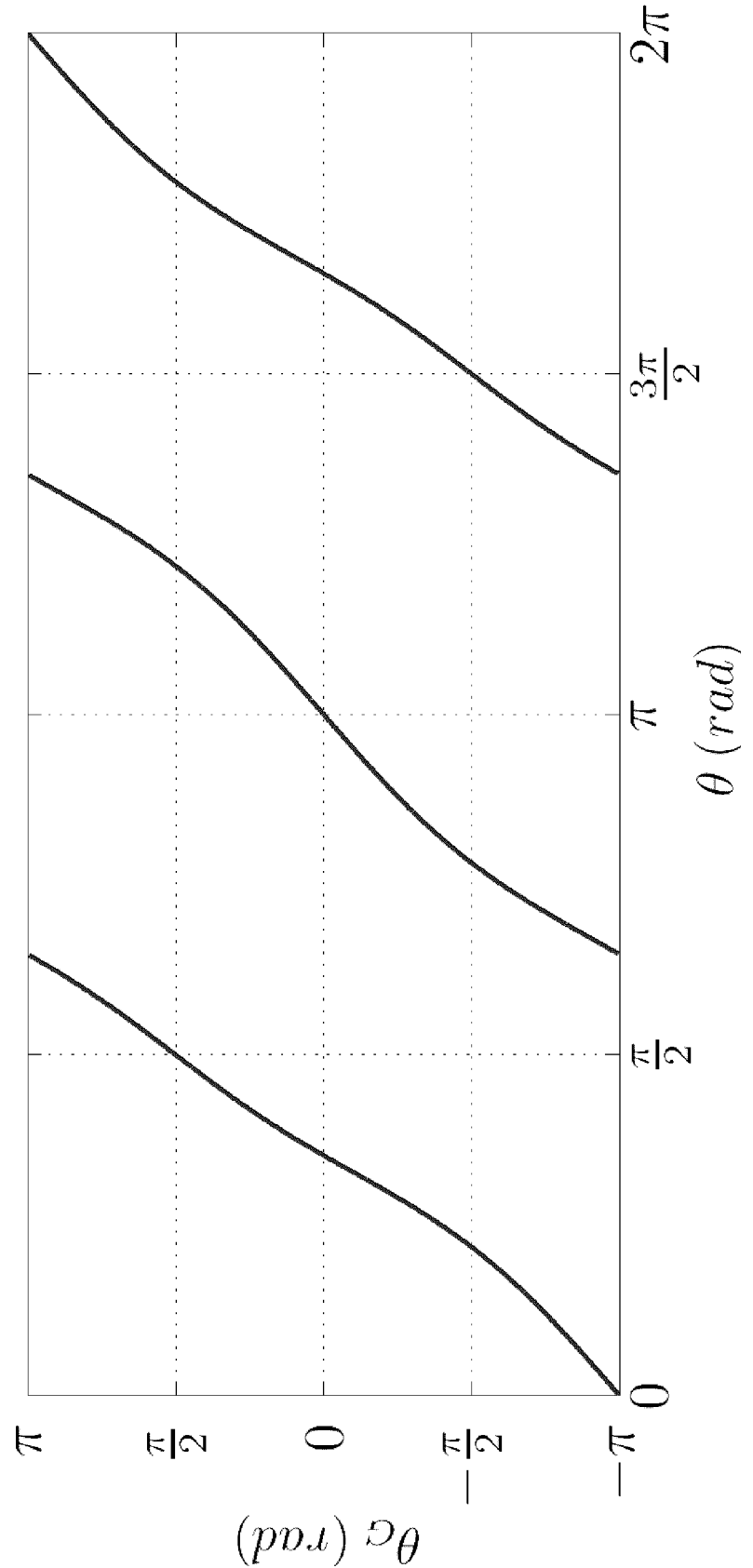
FIG. 3 is a schematic diagram illustrating a plot of the magnetic gradient angle $\theta_G$ as a function of the angle $\theta$ in accordance with a first embodiment of the proposed solution.

Starting from the expression for the magnetic gradient field around a dipole as a function of r, Eq. (12) and Eq. (13), positioning a core includes solving the inverse problem. In other words, positioning a core is sought such that the resultant magnetic gradient G=(G, $\theta_G$, $\varphi_G$) at a target (bifurcation) point p has a given magnitude and orientation. Similar problems have been solved to localize dipoles when the magnetic field and its gradient tensor are known at a certain point by V. Y. Epp, G. F. Kopytov and T. G. Mitrofanova in "Inverse Problem for Static Electromagnetic Field in a Dipole Approximation", ArXiv Phys. e-prints, vol. 3, no. physics/0404081, 2004; and by T. Nara, S. Suzuki and S. Ando in "A Closed-Form Formula for Magnetic Dipole Localization by Measurement of its Magnetic Field and Spatial Gradients", IEEE Trans. Magn., vol. 42, no. 10, pp. 3291-3293, 2006. In the first embodiment, where only the gradient at p is known, the localization problem is ill-posed because for any given gradient, there are always three solutions (see FIG. 2A). In accordance with the first embodiment, the following approach is proposed to calculate and consider these three positions:

The symmetry of the magnetic gradient field around $\hat{z}$ is employed to first solve the inverse problem in 2D. Plane $\Pi$ is defined, centered at p and oriented such that the vectors m and G lie on this plane. Recalling that m is parallel to $\hat{z}$, the orientation of $\Pi$ can be defined, relative to the xz-plane, by a rotation around $\hat{z}$ by the angle $\varphi$. From Eq. (13), the 2D positioning solution will apply on plane $\Pi$:

$$\tan\theta_G = \frac{\sin\theta(1-5\cos^2\theta)}{\cos\theta(3-5\cos^2\theta)} = \frac{a}{b} \quad (14)$$

$$G = \frac{3\mu_G m}{4\pi r^1}\sqrt{a^2+b^2} \quad (15)$$

where the substitution variables a and b are introduced to simplify the latter equation. The relation between $\theta_G$ and $\theta$ in Eq. (14) is plotted in FIG. 3. It is noted that for any orientation of the desired magnetic gradient at p, there are three solutions for $\theta$ (for example as illustrated in FIG. 2A by the circles and/or crosses). Although $\theta$ cannot be isolated in this equation, these solutions can be found numerically by, for example, interpolating precomputed values in a lookup table. Then, calculating the distance r for each value of $\theta$ can be performed by using Eq. (15) resulting in three possible positions of the target (bifurcation) point p relative to the core position. Or, equivalently/inversely, the three possible core positions $d_1^\Pi$, $d_2^\Pi$ and $d_3^\Pi$ relative to p (expressed in Cartesian coordinates) in $\Pi$, are given by:

$$d_i^\Pi = \begin{bmatrix} -e_i\sin\theta_i \\ -r_i\cos\theta_i \end{bmatrix} = \begin{bmatrix} d_{i,x}^\Pi \\ d_{i,z}^\Pi \end{bmatrix} \quad i=1,2,3 \quad (16)$$

It is noted that in 3D, for any angle $\varphi_G$, the three possible core positions lie on the plane $\Pi$. The extension to the 3D solution in the xyz global frame therefore involves a rotation of the 2D positions $d_i^\Pi$ by an angle $\varphi_G$ around $\hat{z}$ and a translation by p:

$$d_2 = R_z(\varphi_G)d_i^\Pi - p \quad (17)$$

$$= \begin{bmatrix} \cos\varphi_G & -\sin\varphi_G & 0 \\ \sin\varphi_G & \cos\varphi_G & 0 \\ 0 & 0 & 1 \end{bmatrix}\begin{bmatrix} d_{i,x}^\Pi \\ 0 \\ d_{i,z}^\Pi \end{bmatrix} + p \quad (18)$$

$$= \begin{bmatrix} d_{i,x}^\Pi \cos\varphi_G \\ d_{i,x}^\Pi \sin\varphi_G \\ d_{i,z}^\Pi \end{bmatrix} - p \quad i=1,2,3 \quad (19)$$

Single Core Positioning Regions

The solution detailed above for the magnetic gradient inverse problem provides finding optimal positions of a core in order to induce a specific gradient at a target (bifurcation) point p. In practice however, placing the core at one of these positions might not be possible due to physical constraints.

In accordance with the proposed solution, a more practical solution includes defining constraints on the desired gradient, in particular a maximum orientation error angle $\xi_{max}$ for the desired orientation $(\theta_G, \varphi_G)$ and a minimum magnitude $G_{min}$. In accordance with the proposed solution, these limit parameters can be defined by taking into account hemodynamic properties, such as blood viscosity and flow velocity, branch (bifurcation) angles and radii of curvature, as well as the magnetic specifications of the injected particles.

Single Core Size

It was previously shown that magnetic gradients in the order of at least 200-400 mT/m are desirable in order to control ferromagnetic therapeutic agents inside blood vessels by J.-B. Mathieu and S. Martel in "Steering of Aggregating Magnetic Microparticles using Propulsion Gradients Coils in an MRI Scanner", Magn. Reson. Med., vol. 63, no. 5, pp. 1336-45, 2010; and by P. Pouponneau, J.-C. Leroux, G. Soulez, L. Gaboury and S. Martel in "Co-encapsulation of Magnetic Nanoparticles and Doxorubicin into Biodegradable Microcarriers for Deep Tissue Targeting by Vascular MRI Navigation", Biomaterials, vol. 32, no. 13, pp. 3481-6, 2011, both of which are incorporated herein by reference. Because the gradient magnitude around a dipole decreases at a fast rate as $1/r^4$, it is of interest to investigate how far from a core such gradient magnitudes can be obtained.

More relevant for the following, we define h, the distance of a particle from the core surface:

$$h = r - R_{core} \quad (20)$$

The gradient magnitude varies, for a fixed distance (h), as a function of $\theta$. Using Eq. (15), the maximum gradient $$G = 2\frac{3\mu_0 m}{4\pi r^4}$$

is obtained at $\theta=0$ and $\theta=\pi$, whereas the minimum gradient $$G \approx 0.9\frac{3\mu_0 m}{4\pi r^4}$$

occurs at $\theta \approx \pm 0.352\pi$ and $\theta \approx \pm 0.648\pi$. The gradient magnitude is also function of the core magnetic moment, which depends on the total volume of the core and the material used according to Eq. (3). In accordance with the proposed solution, a soft ferromagnetic material having a volume magnetization M as high as possible can be used. For such a material, the gradient magnitude at a distance h is function of the core size.

Figure 4A:
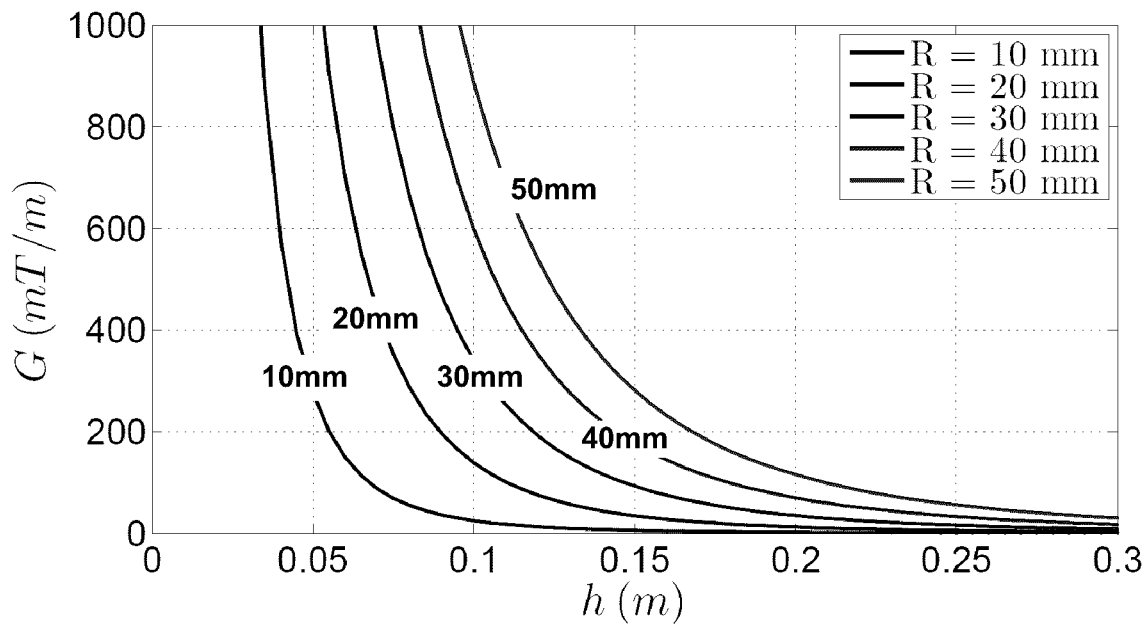
FIG. 4A is a schematic diagram illustrating a plot of theoretical maximum gradient magnitude for carbon steel of different sizes in accordance with the proposed solution.
Figure 4B:
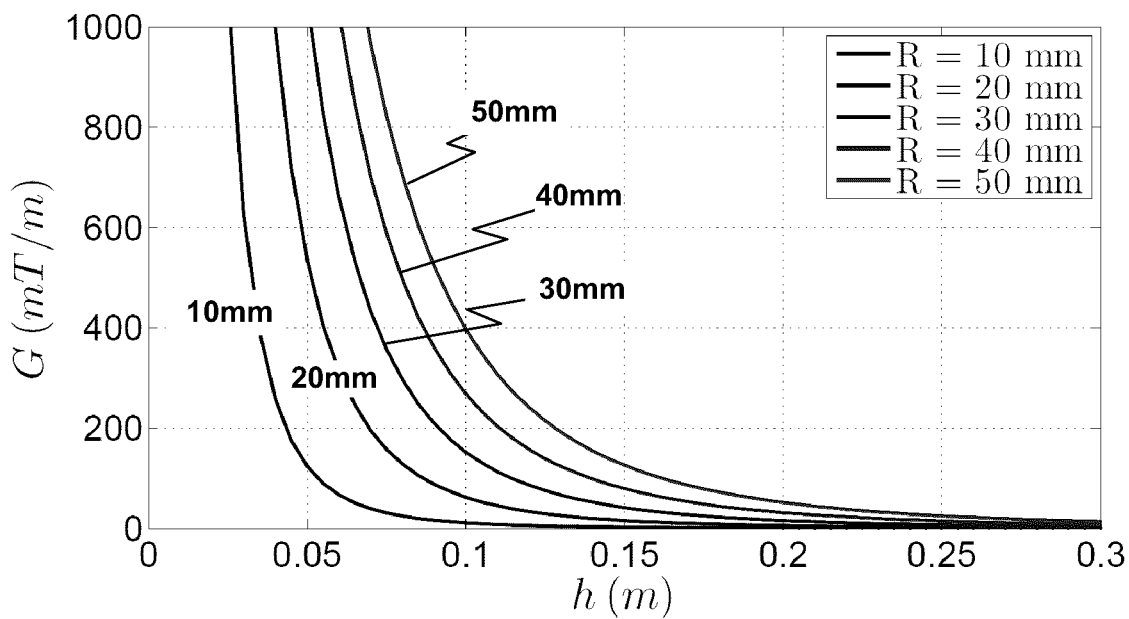
FIG. 4B is another schematic diagram illustrating a plot of theoretical minimum gradient magnitude for carbon steel of different sizes in accordance with the proposed solution.

FIGS. 4A and 4B illustrate sample plots of theoretical maximum and minimum gradient magnitudes, calculated at $\theta=0$ and $\theta=0.352\pi$ respectively, using Eq. (15), as a function of h for different spherical core radii. The illustrated curves have been found to correspond carbon steel balls magnetized at 1.5 T, for which the volume magnetization is $M_{1.5T}=1.43\times 10^6$ A/m. At h=10 cm from the core surface, which distance would allow to reach most regions inside a subject's body (patient). It is noted that a core of radius R=3 cm can be sufficient to produce a gradient of more than 300 mT/m in the best case ($\theta=0$). To ensure a minimum gradient of the same magnitude in the worst case ($\theta \approx 0.352\pi$) however, a core of radius between 4 cm and 5 cm can be employed.

Experimental Implementation of the First Embodiment of the Proposed Solution

The feasibility of endovascular navigation using the proposed method was tested in vitro by attempting to control (induce deflection) the propagation direction of magnetic particles at a fluid junction, in accordance with an implementation of the first embodiment of the proposed solution.

An experimental setup included a T-shaped glass tube, having a constant circular cross-section of 3 mm in diameter, splitting in two branches: one going straight and one branching (bifurcating) at a 90° angle. The input of the tube was connected to a syringe pump (Harvard Apparatus PHD 2000™) delivering a constant flow of 60 ml/min, which is representative of some arterial blood flow in (the human) body. This yielded an average flow velocity of 14 cm/s before the junction. The pulsating nature of blood flow was considered in terms of average flow as a simplification to the setup. For example, a solution of 36% (vol.) glycerol in water having a dynamic viscosity of 3.5 mPa·s can be used as a blood-analogue fluid (for example as in "Pulsatile Flow Studies of a Porcine Bioprosthetic Aortic Valve in vitro: PIV Measurements and Shear-Induced Blood Damage" by W. L. Lim, Y. T. Chew, T. C. Chew and H. T. Low, J. Biomech., vol. 34, no. 11, pp. 1417-27, 2001).

The T-shaped tube was fixed on a LEGO® baseplate and centered in the tunnel of a Siemens Avanto™ MRI scanner having a static field density of about $B_0$=1.5 T. The tube was oriented such that it was parallel to the horizontal xz-plane, with the two branches (bifurcations) angled at 45° from {circumflex over (z)}. A carbon steel spherical core of radius $R_{core}$=12.7 mm, having a volume magnetization $M_{1.5T}$=1.43×10⁶ A/m at 1.5 T, was glued onto a pile of LEGO® blocks, which provided the ability to quickly and precisely change the core position on the baseplate during the experiments. The core center was substantially aligned vertically with the center of the T-shaped tube (along the y-axis). The core could then be positioned according to the baseplate grid, defined by a stud spacing of 8 mm. The core was considered to have saturated in terms of magnetization, as its magnetization at 1.0 T, $M_{1.0T}$=1.4.1×10⁶ A/m, is about 1.3% less than $M_{1.5T}$.

In order to test the proposed method, guiding magnetic particles inside each of the branches (bifurcations) as attempted separately. The arrangement of the setup allowed solving the core positioning problem in 2D for simplicity. It is emphasized that the sets of 2D core positions (positioning regions) respecting the constraints on the desired gradient can be found and tested in this experiment for the first embodiment of the proposed solution, in general the sets of core positions define closed volumes as described herein below with respect to the second embodiment of the proposed solution.

Figure 5B:
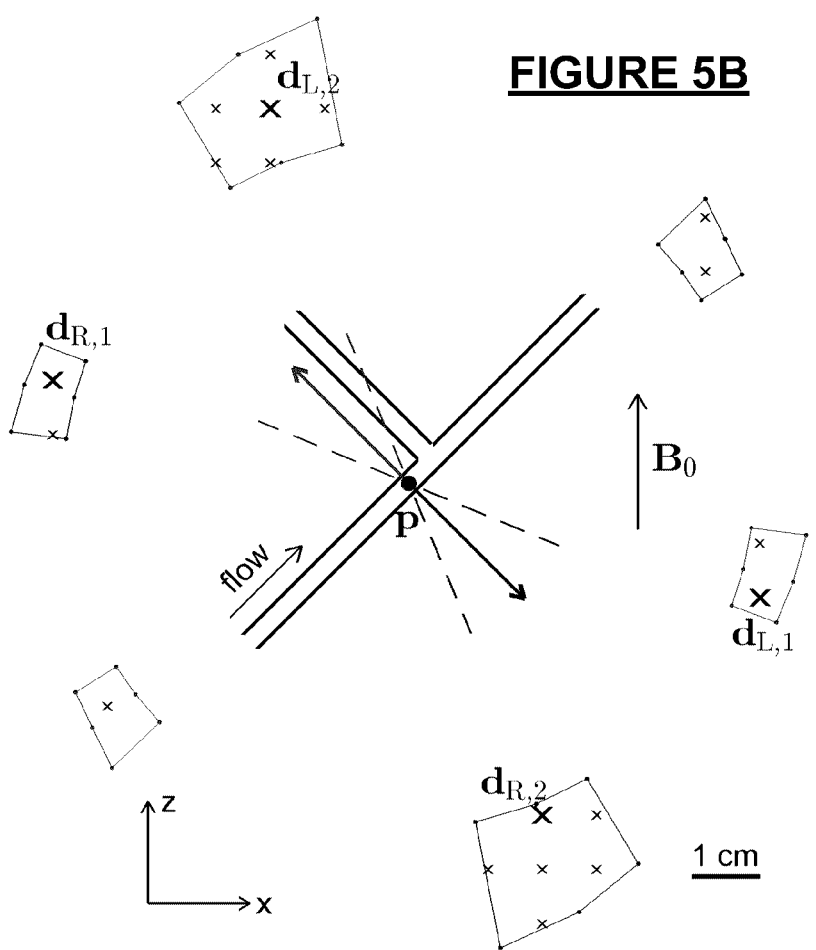
FIGS. 5A and 5B are schematic diagrams illustrating core positioning regions and respectively for magnetic particle deflection in orthogonal branches in accordance with a first embodiment of the proposed solution.
Figure 5A:
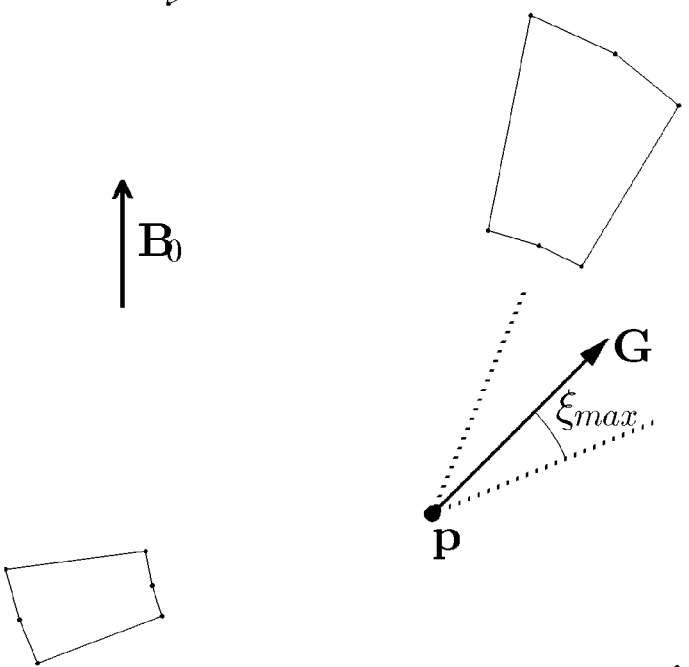
Figure 6A:
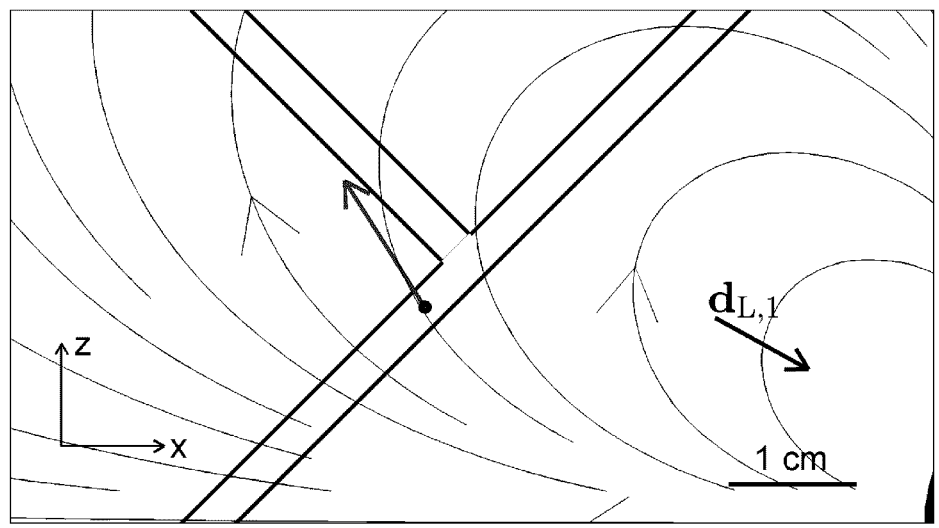
FIGS. 6A, 6B, 6C and 6D are schematic diagrams illustrating solution details at positions $d_{L,1}$, $d_{L,2}$, $d_{R,1}$ and $d_{R,2}$ of FIG. 5B, in accordance with an implementation of the first embodiment of the proposed solution.
Figure 7A:
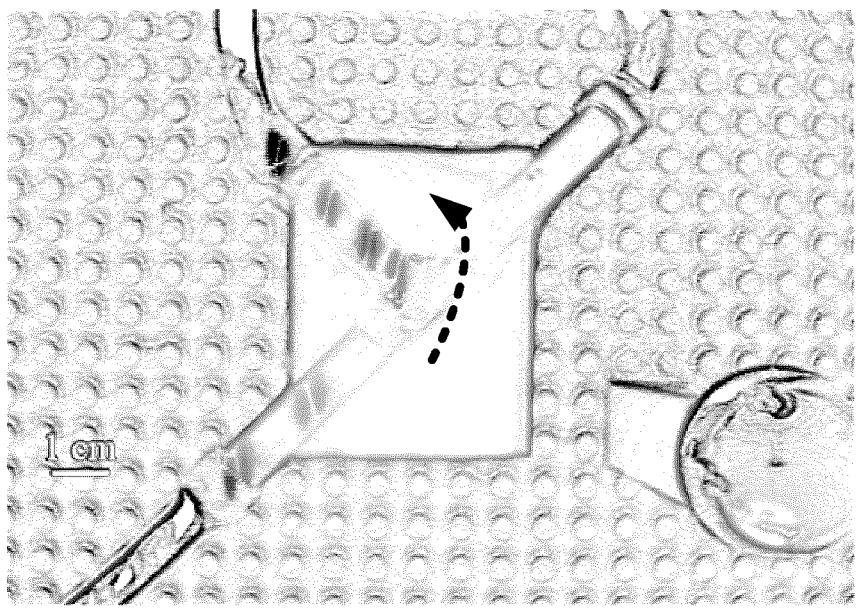
FIGS. 7A, 7B, 7C and 7D are schematic diagrams respectively illustrating sample video frames showing fluid flow corresponding to core position solutions $d_{L,1}$, $d_{L,2}$, $d_{R,1}$ and $d_{R,2}$ of FIG. 5B in accordance with the implementation of the first embodiment of the proposed solution.
Figure 8A:
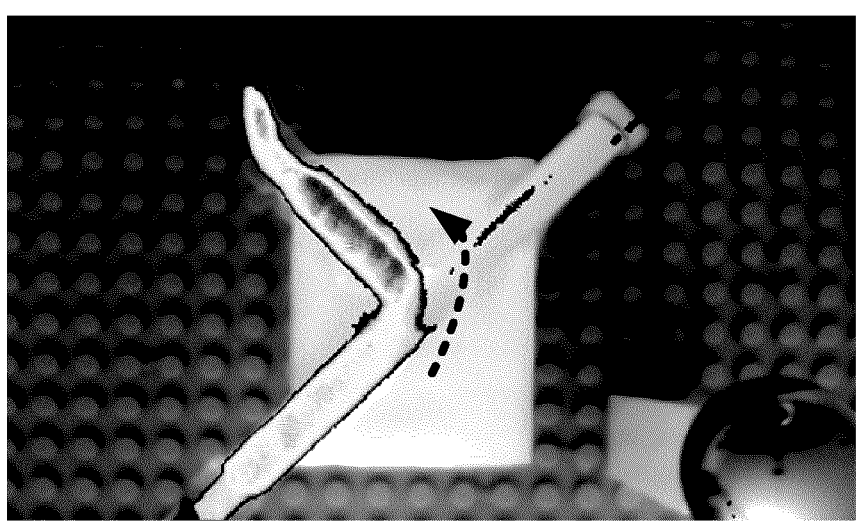
FIGS. 8A, 8B, 8C and 8D are schematic diagrams respectively illustrating navigation results obtained by positioning the core at positions $d_{L,1}$, $d_{L,2}$, $d_{R,1}$ and $d_{R,2}$ of FIG. 5B, in accordance with yet another embodiment of the proposed solution.
Figure 6B:
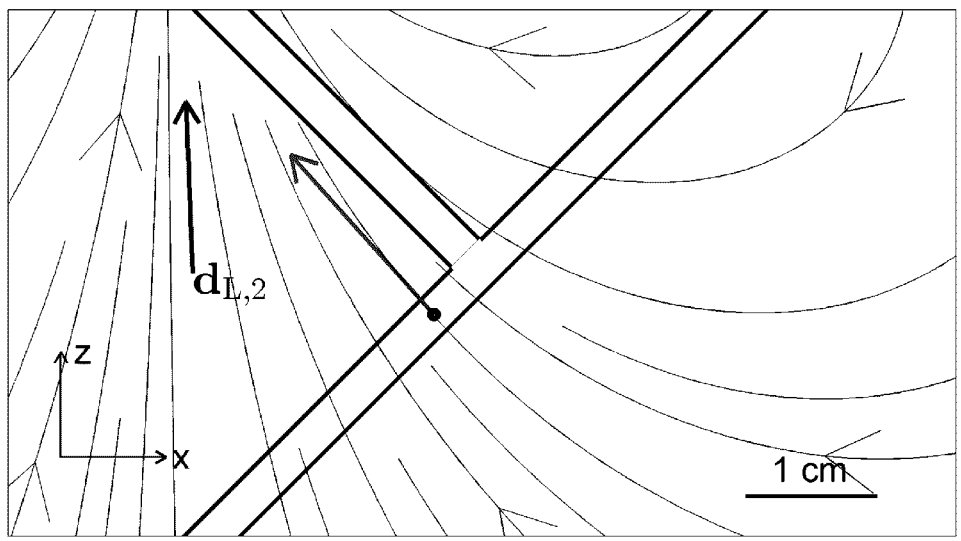
Figure 7B:
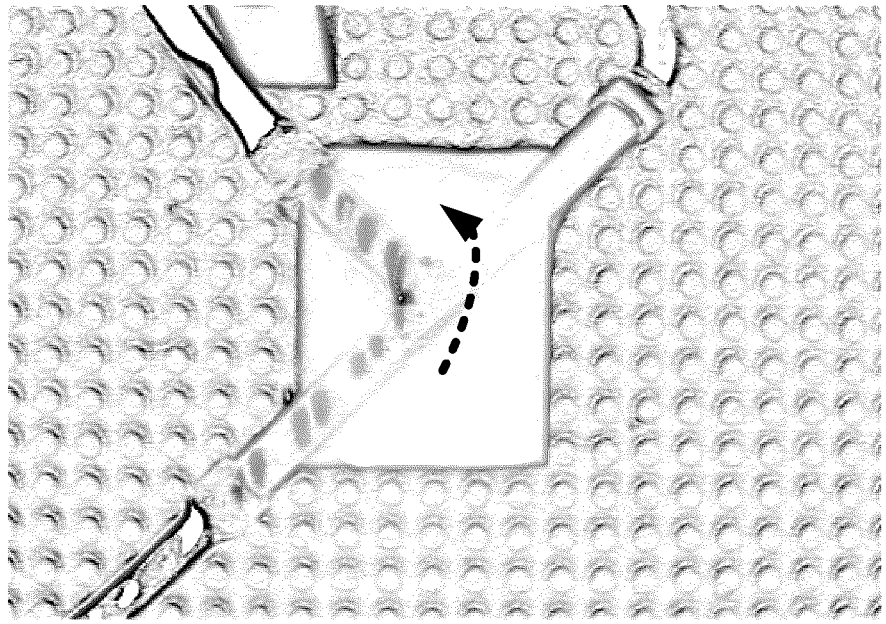
Figure 8B:
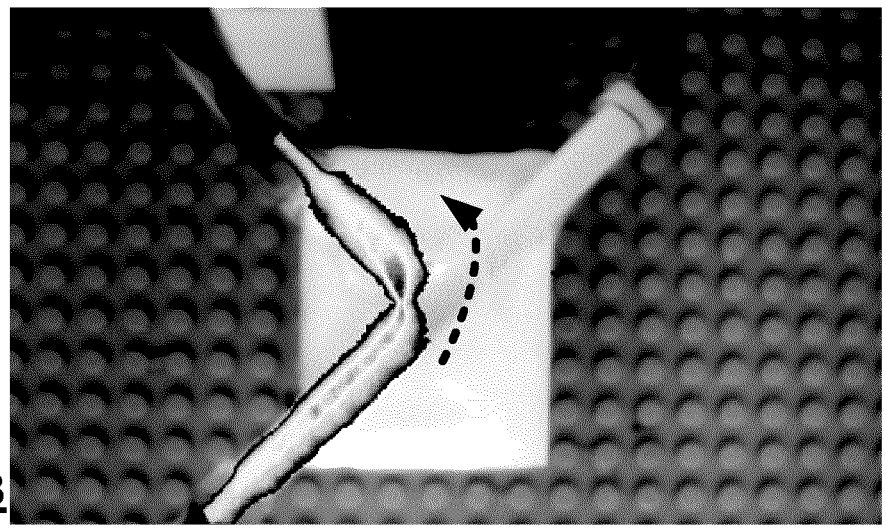
Figure 6C:
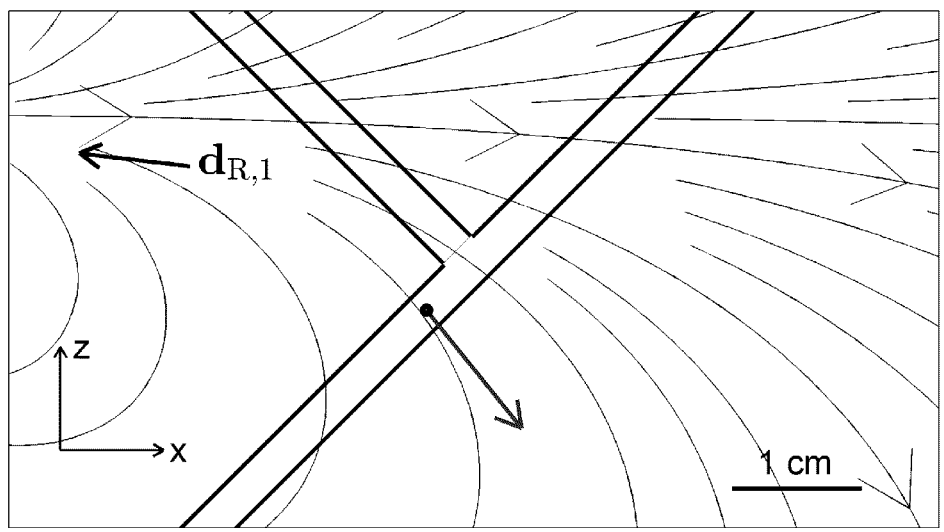
Figure 7C:
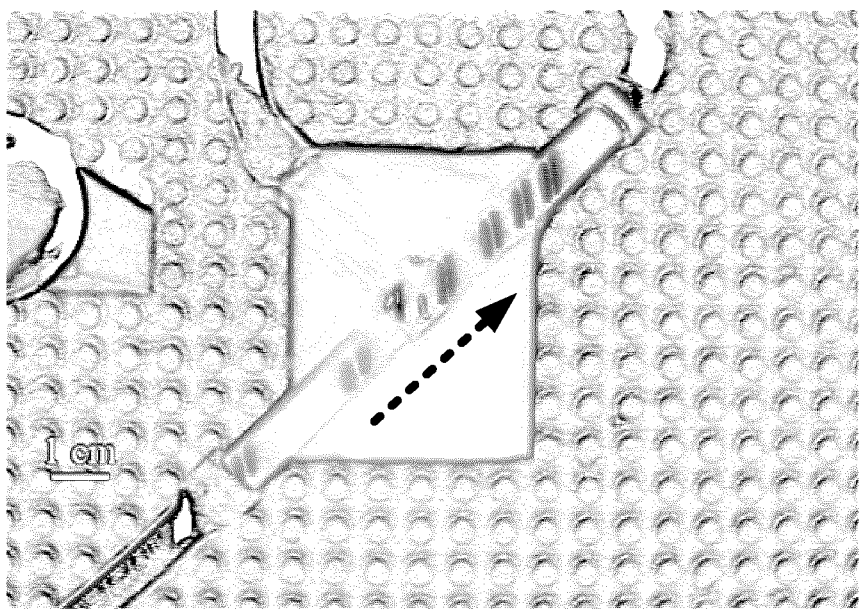
Figure 8C:
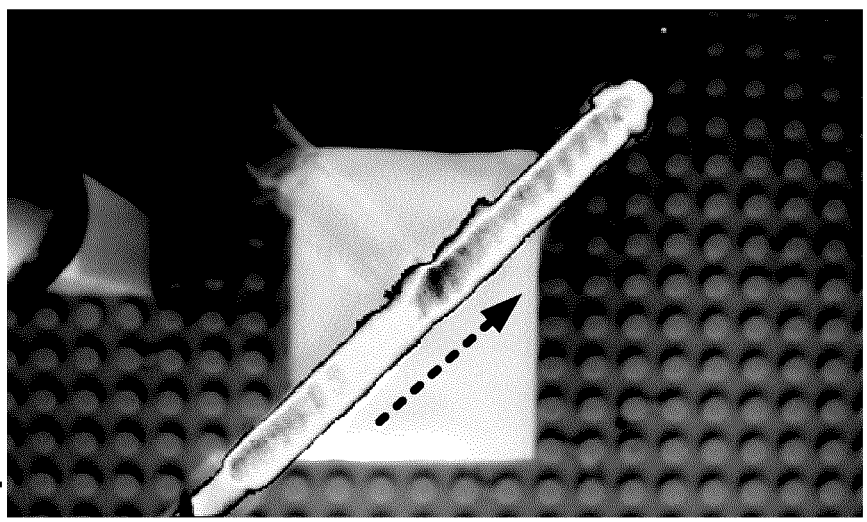
Figure 6D:
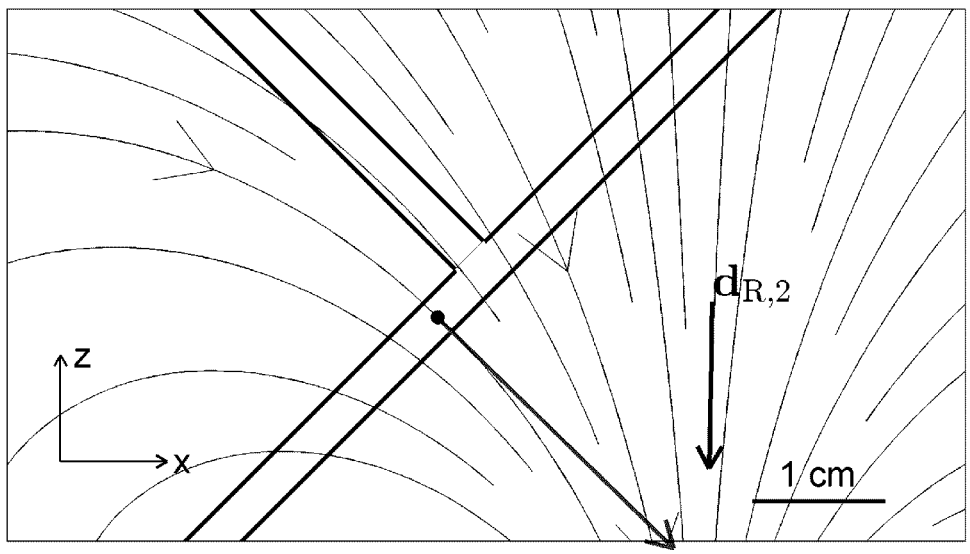
Figure 7D:
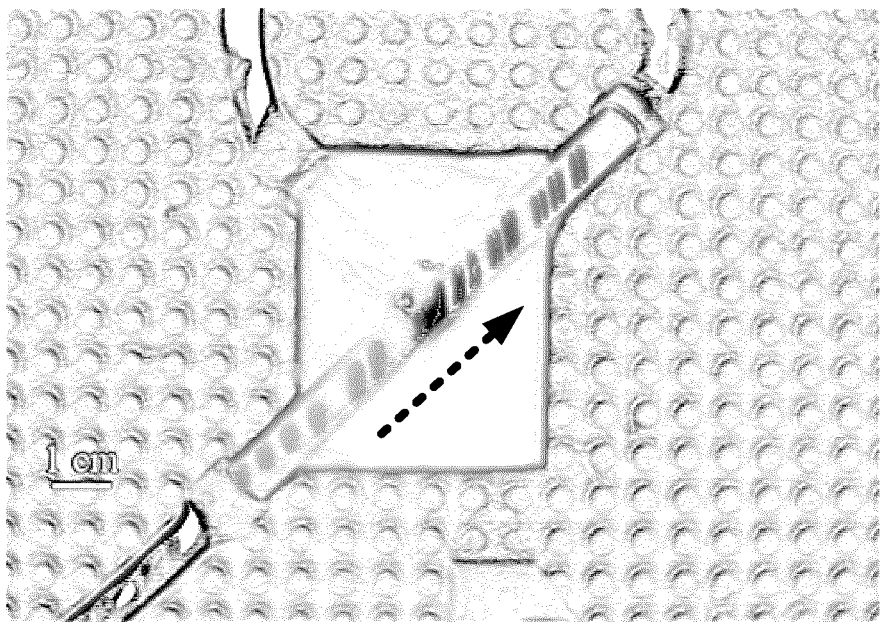
Figure 8D:
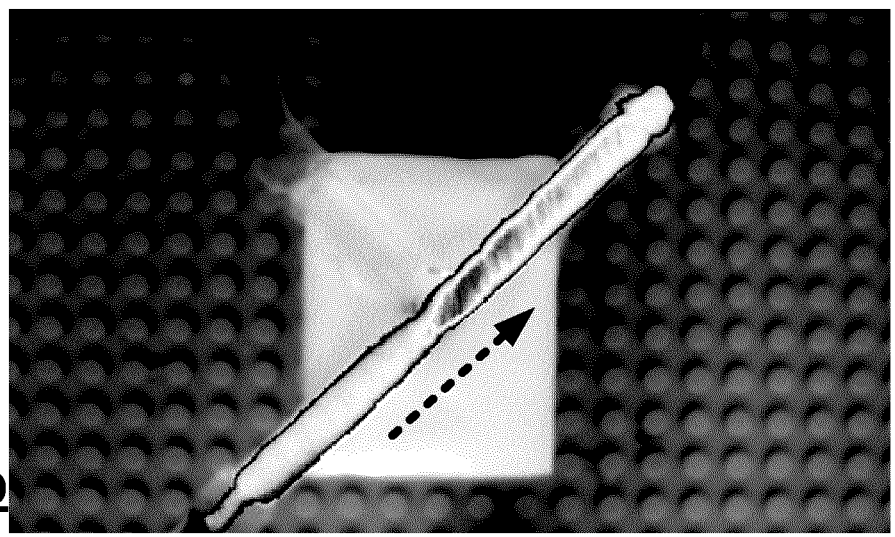

Returning to the implementation of the first embodiment of the proposed solution, the target point was set 5 mm upstream of the junction center (for tube diameter 3 mm). The desired gradient orientations were defined as $\theta_G=-\pi/4$ and $\theta_G=3\pi/4$ for the left and right branches (bifurcation) respectively. It is noted that each of these gradients are orthogonal to the flow in the order branch to push/pull (force) the particles on the desired side of the tube, past the centerline, as detailed by J.-B. Mathieu and S. Martel in "Steering of Aggregating Magnetic Microparticles using Propulsion Gradients Coils in an MRI Scanner", Magn. Reson. Med., vol. 63, no. 5, pp. 1336-45, 2010, which is incorporated herein by reference. FIG. 5A illustrates arrows depicting the desired gradient orientations at $G_{min}$=300 mT/m, while dashed lines depict the gradient orientation errors corresponding to $\xi_{max}=\pi/8$. In FIG. 5B, core positioning regions (surfaces) corresponding to each branch (bifurcation) are also illustrated respecting the constraint $r/R_{core}>4$. The surface vertices were obtained by calculating the core positions corresponding to the constraint limits. The matching core positions on the LEGO® baseplate are marked by small gray crosses. Four of these positions were tested, two per branch (bifurcation), which are identified by larger crosses. For reference herein, the tested positions are identified as $d_{L,1}$, $d_{L,2}$ and $d_{R,1}$, $d_{R,2}$ for deflecting (sending) particles in the left and right branches (bifurcations) respectively. The two remaining positioning regions could not be tested due to the core colliding with the glass tubing at these positions. It is appreciated that core collision with the glass tube is a limitation of the experimental setup of the implementation and not of the proposed solution.

For each of the tested positions, ferrofluid was injected upstream of the T-shaped tube in order to introduce magnetic particles in the flow. Using ferrofluid Ferrotec™ EFH1 having a volume magnetization $M_{1.0T}$=17240 A/m at 1.0 T and $M_{1.5T}$=17580 A/m at 1.5 T (2% increase) was considered to be saturated at 1.5 T. When injected, the ferrofluid formed small aggregations in the direction of $B_0$. A MRI-compatible camera (MRC Systems GmbH model 12M) was placed above the junction and recorded the motion of the ferrofluid aggregations during the injection with 640×480 pixel resolution and 30 frames per second. The average video duration over each of the four tested positions was 19 s. A differential analysis was performed on each video sequence in order to detect moving aggregates from frame to frame.

FIGS. 6A, 6B, 6C and 6D respectively illustrate solution details at positions dL,1, dL,2, dR,1 and dR,2 of FIG. 5B. The first row depicts the calculated gradient field around the junction and the theoretical resulting gradient at p.

FIGS. 7A, 7B, 7C and 7D respectively illustrate sample video frames showing fluid flow corresponding to core position solutions. The second row shows raw images from the videos. FIGS. 8A, 8B, 8C and 8D respectively illustrate ferromagnetic particle navigation results obtained by positioning the core at dL,1, dL,2, dR,1 and dR,2. The third row shows images from the videos with corresponding motion density plots of the detected motion superimposed on average video frame. On the latter, areas of highest motion density are shaded and motion is illustrated with arrows. Experimental positioning of the core is visible in FIGS. 7A, 7C, 8A and 8C.

In each of these tests, the navigation attempt was successful as the results show the ferrofluid aggregates being deflected (bifurcating) in the desired branch. In the corresponding video, tiny boluses (≈10-20 times smaller than the other aggregates) were observed veering (bifurcating) in the wrong branch. In particular, motion was detected substantially only in the desired branch for core positions $d_{L,2}$, $d_{R,1}$ and $d_{R,2}$. For core position $d_{L,1}$, a region of low motion density was observed in the wrong branch. While such tiny boluses were observed in the wrong branch for $d_{L,1}$ these were not significant enough to appear on the corresponding motion density plot. A single tiny bolus was seen taking the wrong branch for $d_{R,1}$ and none for $d_{R,2}$.

Although the targeting efficiency was not quantified, based on these visual results it was found that the vast majority of the ferrofluid aggregates were guided successfully in the desired branch (bifurcation). This clearly demonstrates that it is possible to control the propagation direction of magnetic particles at a vessel junction using the proposed method.

By adequately positioning ferromagnetic cores inside the tunnel of a MRI system, magnetic gradients can be generated by distortions in the otherwise uniform field to entail the therapeutic agents to follow a prescribed (precise) path in a vascular network towards a targeted region to be treated. The high field strength inside the tunnel of the MRI scanner can be sufficient to bring the magnetization of both the cores and the navigable therapeutic agents close to or at full saturation magnetization. This principle of operation of the endovascular navigation method of the first embodiment of the proposed solution was demonstrated experimentally. DFN can provide high directional gradients comparable to the ones generated by other expensive and complex electromagnetic coil assemblies, while the responsiveness of the therapeutic agents to the applied gradients is increased. DFN preliminary in vitro experimental results using one core in a 1.5 T MRI scanner confirms the potential of DFN for targeted drug delivery.

It is noted that in accordance with the first embodiment of the proposed solution, the proposed method to predict the effect of the cores on the navigable agents makes no recourse to switching (dynamically changing) gradients, which are limited in their slew (transition) rate due to technological and/or physiological constraints (e.g. safety issues such as peripheral nerve stimulation for the patient) and other limiting factors such as overheating coils.

Second Embodiment of the Proposed Solution

In accordance with a second embodiment of the proposed solution, directional gradients are generated by positioning multiple soft ferromagnetic cores at specific locations around the patient positioned inside the tunnel of a clinical MRI scanner. Placing a patient in the tunnel of a clinical MRI scanner, as in MRN, the MNPs reach their saturation magnetization and high gradients are generated by the distortions of the scanner's homogeneous field from appropriately sized ferromagnetic cores placed at specific locations outside the patient. These cores of a few centimeters in diameter induce a distortion of the uniform field in the scanner, which creates a magnetic path followed by the therapeutic agents.

The addition of the field $B_{core}$ to the external field $B_0$ induces a distortion of the total magnetic field around the core. This distortion generates magnetic gradients that can be used to induce directional forces on magnetic particles circulating in the vicinity of the core. For a particle of magnetic moment $m_p$, the magnetic force due to multiple cores is given by:

$$F_{mag} = \nabla(m_p \cdot B_{tot}) \quad (21)$$

where $B_{tot} = B_1 + B_2 + \ldots + B_N$ is the summation of the magnetic fields generated by N cores. The field $B_0$ can be omitted from the equation since it is homogeneous.

When the magnetic dipole-dipole interactions between cores, and between cores and particles are negligible, Eqs. (2) and (3) hold and all the magnetizations are approximately parallel to $B_0$. This assumption can be respected for DFN, in practice as explained hereinbelow. Letting $B_0 = B\hat{z}$ be aligned with the z-axis Eq. (21) simplifies to:

$$F_{mag} \approx m_p \nabla B_{tot} = m_p G_{tot} \quad (22)$$

which means that the force exerted on a magnetic particle depends on the gradient $G_{tot}$ of the z-component of $B_{tot}$ at the particle's location.

For a core with $m = m\hat{z}$, Eq. (2) can be expressed as:

$$B = \frac{\mu_0 m}{4\pi r^4}[3xz\hat{x} + 3yz\hat{y} + (3z^2 - r^2)\hat{z}] \quad (23)$$

Figure 1B:
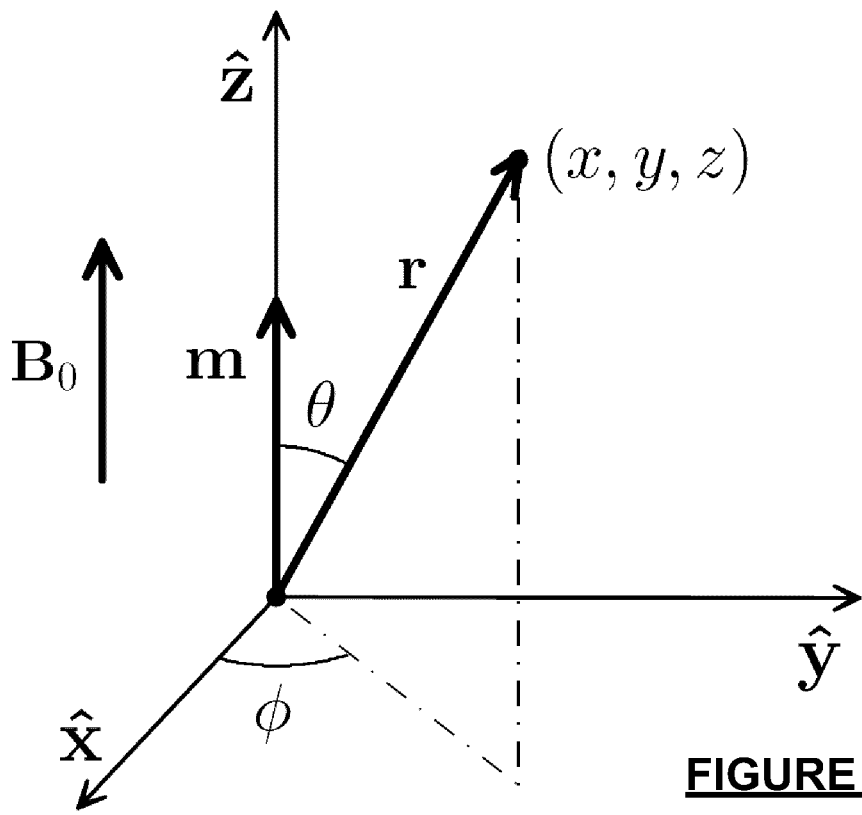
Figure 2B:
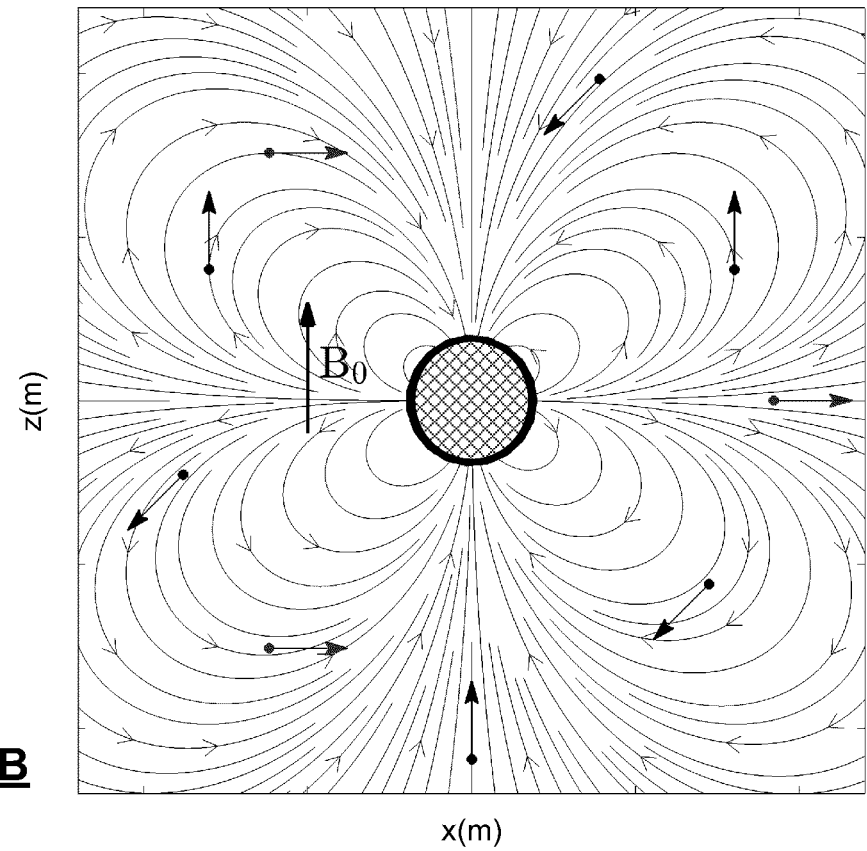

This gradient field is symmetric around $\hat{z}$, as illustrated in FIGS. 2A and 2B. Calculating the gradient of $B_z$ yields:

$$G = \nabla\left(\frac{\mu_0 m}{4\pi} \frac{3z^2 - r^2}{r^5}\right) \quad (11)$$

$$= \frac{3\mu_0 m}{4\pi r^7} \begin{bmatrix} x(r^2 - 5z^2) \\ y(r^2 - 5z^2) \\ z(3r^2 - 5z^2) \end{bmatrix}^T$$

which for later convenience is converted to spherical coordinates, as done in respect of Eq. (12), using the convention illustrated in FIG. 1B:

$$G = \frac{3\mu_0 m}{4\pi r^4} \begin{bmatrix} \sin\theta\cos\phi(1 - 5\cos^2\theta) \\ \sin\theta\sin\phi(1 - 5\cos^2\theta) \\ \cos\theta(3 - 5\cos^2\theta) \end{bmatrix}^T \quad (24)$$

with $r = (r, \theta, \varphi)$ defined relative to the center of the core.

Employing the superposition principle, the total gradient resulting from N magnetized cores is given by:

$$G_{tot} = \sum_{n=0}^{N} G_n \quad (25)$$

From the above equations, a set of adequately positioned ferromagnetic cores are expected to generate a predefined magnetic gradient field that would deflect (entail) magnetic agents to follow a desired path in a vascular network. Such positioning of multiple cores is subject to physical constraints. In particular, cores cannot overlap on each other or be positioned inside the patient's body.

Magnetic Interactions

Magnetic dipole-dipole interactions are possible in DFN if two magnetized cores are located close to each other. Such interactions can not only induce strong attractive or repulsive forces between the cores, but can also alter the magnitude and orientation of the magnetization of the core material itself. This alteration can lead to the inaccuracy of the analytical models such as (2) and (3). For example, the actual average magnetization of two spheres in an attractive mode may be underestimated, whereas in a repulsive mode the actual average magnetization may be overestimated. No analytical models exist to calculate the magnetization of cores under interactions in general, thus these calculations are only available from numerical simulations.

Dipole-dipole interactions have been studied, for example for the calculation of attractive or repulsive forces between magnetized cores (R. Castañer, J. M. Medina, and M. J. Cuesta-Bolao in "The Magnetic Dipole Interaction as Measured by Spring Dynamometers", Am. J. Phys., vol. 74, no. 6, pp. 510-513, 2006; Y. Kraftmakher in "Magnetic Field of a Dipole and the Dipole-Dipole Interaction", Eur. J. Phys., vol. 28, no. 3, pp. 409-414, May 2007; and A. Mehdizadeh, R. Mei, J. F. Klausner and N. Rahmatian in "Interaction Forces Between Soft Magnetic Particles in Uniform and Non-Uniform Magnetic Fields", Acta Mech. Sin., vol. 26, no. 6, pp. 921-929, 2010). In particular, Mehdizadeh et al. have shown that the magnetic dipole approximation for two identical soft ferromagnetic spheres immersed in an external field is reasonably accurate for r/R>4, where r is the center-to-center distance between the spheres. Their work however addressed the case where the magnetizations of the spheres lie within the linear zone of the magnetization curve (M-H), where the variation of M is the largest. In accordance with the proposed solution, because the cores are close to or at full saturation magnetization (i.e., on the plateau region of the M-H curve), it is expected that the interaction effects on the validity of the models presented herein could be less significant and thus the dipole approximation limit could be set at a closer distance between the cores. Nevertheless, since the problem of dipole-dipole interactions is addressed separately (see further embodiments hereinbelow), here the r/R>4 limit is used as a constraint for the purpose of this second embodiment of the proposed solution. This constraint is conservatively used to define the "far enough" criterion.

The method for positioning a single core presented hereinabove is recalled as it constitutes the basis for the multi-core positioning method proposed for the present embodiment.

Letting $G=(G, \vartheta, \varphi)$ be the magnetic gradient desired at a point $p=(x, y, z)$ in space, where $\vartheta$ and $\varphi$ are the $\theta$ and $\phi$ and equivalents used for the notation of a gradient orientation. As depicted in FIG. 2B, for any given G, there are always three positions around a spherical core where this gradient is met. The (ill-posed) problem of positioning a core requires the inversion of Eq. (11) in order to find these three possible solutions.

By exploiting the symmetry of the gradient around $\hat{z}$, this inverse problem can first be solved in 2D in the xz-plane and then extended to 3D by performing a rotation of the solutions around the z-axis. From Eq. (24), the gradient angle $\vartheta$ is related to the angle $\theta$ by:

$$\tan\vartheta = \frac{\sin\theta(1 - 5\cos^2\theta)}{\cos\theta(3 - 5\cos^2\theta)} = \frac{a}{b} \quad (26)$$

The three values $\theta_i$ solving this equation for any given gradient angle $\vartheta$ can be found numerically (e.g., by interpolating in a lookup table). Then, the corresponding values of r are $$r_i = \left[\frac{3\mu_0 m}{4\pi G}\sqrt{a_i^2 - b_i^2}\right]^{1/4} \quad (27)$$

The positions where the gradient G is found around the core are thus (in Cartesian coordinates in the xz core's local frame):

$$r_i = \begin{bmatrix} r_i\sin\theta_i \\ r_i\cos\theta_i \end{bmatrix} \quad (i = 1, 2, 3) \quad (28)$$

The core positions $d_i=(x_i, y_i, z_i)$ in the 3D global reference frame are found by rotating solutions from Eq. (28) by the angle $\varphi$ around $\hat{z}$ and translating them by p:

$$d_i = R_z(\varphi)\begin{bmatrix} -r_i\sin\theta_i \\ 0 \\ -r_i\cos\theta_i \end{bmatrix} + p \quad (i = 1, 2, 3) \quad (29)$$

where $R_z(\varphi)$ is the rotation matrix around the z-axis.

Notice that the gradient magnitude is not constant as a function of $\theta$ for a fixed distance r. In fact, it is maximized at $\theta=0$ and $\theta=\pi$, whereas it is minimized at $\theta\approx\pm0.352\pi$ and $\theta\approx\pm0.648\pi$.

Multi-Core Positioning

Although in some situations navigating two or more fluid junctions (bifurcations) may be possible using one core, in general, single-core DFN-S provides navigation of magnetic agents in one junction (bifurcation). In order to control particles through multiple consecutive junctions (bifurcations) in the general case, using multiple cores is proposed to generate the required field of gradients. In accordance with the second embodiment of the proposed solution, the magnetic path to be created is simplified as a set of "target gradients", defined at some points along the desired vascular path. The following addresses the multi-core DFN-S positioning problem for generating such gradients.

A target gradient is defined as $\mathcal{T} = \{p, G, \xi_{max}\}$, meaning that a magnetic gradient $G=(G_{min}, \vartheta, \varphi)$ is required at location $p=(x, y, z)$ in space, where $\xi_{max}$ is the maximum tolerance angular error (limit threshold) on the gradient orientation and $G_{min}$ is the minimum gradient magnitude (limit threshold). Hereinafter, the target gradient's location p is also called the target point. It is noted that $\xi_{max}$ and $G_{min}$ act as bounding constraints (limit thresholds), meaning that correct core positions for this target gradient point can be represented by closed regions in space (see FIG. 5A). A minimum distance r is also required to avoid the overlapping of the core on the target point, which narrows these positioning regions. The dipole approximation limit constraint r/R>4 considered imposed.

When positioning regions of different target gradients partially overlap, a single core positioned in the intersection area can generate gradients that are within the tolerance of both desired gradients. In this case, the position of the core can be calculated directly. Conversely, when multiple cores are needed, the positioning problem becomes much more complex due to the cumulative contribution of each core to the total gradients. In fact, this problem cannot be solved directly, can be highly nonlinear, and the solution may not be unique.

An important challenge of DFN lies in the development of the models needed to predict the effect of the cores on the agents being navigated. In particular, in order to account for variations of the anatomy between patients and to be adapted in general to any targeted region. The main challenge of DFN lies in the methods required to adequately place multiple cores in an MRI tunnel, a method is needed to find working combinations of core positions and characteristics based on a desired path in a vascular network.

In accordance with the second embodiment of the proposed solution, multiple cores are employed to distort the magnetic field. A method is provided to solve the inverse magnetic problem of positioning a set of cores so that microscale therapeutic agents could be guided through a desired path in the vascular network. The following multi-core positioning method combines nonlinear optimization and tree search in order to find working configurations of cores given a set of target gradients.

Optimization Solution Formulation

Let $G'=(G_{min}', \vartheta', \varphi')$ be the actual total magnetic gradient at a target point, resulting from a certain core configuration $\{C_1, C_2, \ldots, C_N\}$, where a core $C_n=\{d_n, R_n, M_n\}$ is defined by its position $d_n$, its radius $R_n$ and its volume magnetization $M_n$. The error angle $\xi$ is the angle between the vector G' and the desired gradient G.

The general optimization solution is formulated by positioning N cores to generate a set of K target gradients $\{T_1, T_2, \ldots, T_K\}$ as the maximization of the normalized vector projections of all $G'_k$ on their respective $G_k$, that is:

$$X^* = \underset{X}{\operatorname{argmax}} \sum_{k=1}^{K} \frac{G'_k \cdot G_k}{\|G'_k\| \|G_k\|} = \underset{X}{\operatorname{argmax}} \sum_{k=1}^{K} \cos\xi_k \quad (30)$$

where $\chi^*$ denotes the set of optimal (unknown) positioning parameters $\chi=\{d_1, d_2, \ldots, d_N\}$, subject to the constraints $$G'_k \geq G_{min,k} \quad \forall k \in [1, K] \quad (31)$$

$$\|d_n - P_k\| \geq 4R_n \quad \forall n \in [1, N], \forall k \in [1, K] \quad (32)$$

$$\|d_n - d_m\| \geq 4\max(R_n, R_m) \quad \forall n, m \in [1, N]/n \neq m \quad (33)$$

Maximizing the objective function corresponding to Eq. (30) minimizes the error angles $\xi$, with more emphasis on large errors. The gradient magnitudes are excluded from the objective function to avoid the compensation of a bad gradient orientation (large $\xi_k$) by a greater gradient magnitude $G_k'$. Instead, $G_{min}$ values are enforced (provided) by the constraints in Eq. (31).

The constraints in Eqs. (32) and (33) arise from the aforementioned dipole approximation limit r/R>4. Constraints in Eq. (32) allow accurately prediction of the magnetization of the magnetic particles when they reach a target point. The largest of two cores is considered to compute the minimum separating distances. Note that even without the dipole approximation limit, these two constraints would be necessary to avoid physically unfeasible core placements. The minimum value of the right-hand sides of the inequalities would then be $R_n$ for Eq. (32) and $R_n+R_m$ for Eq. (33).

Other constraints can be defined in addition to Eqs. (31) and (33) to ensure that the cores lie outside the patient's body. Finally, the optimization of Eq. (30) is considered as successful when the resulting errors $\xi_k$ are bellow their respective $\xi_{max,k}$ values.

Alternating Optimizations

The above optimization problem is nonlinear and non-convex. In accordance with the proposed solution, to reduce its complexity when multiple cores are involved, a proposed methods includes optimizing Eq. (30) using an Alternating Optimization (AO) method. Such a method is explained with reference to the search algorithm described hereinbelow.

Alternating Optimization includes successively optimizing an objective function with respect to individual non-overlapping parameter subsets, $S_1, S_2, \ldots, S_N$, while the remaining parameters are fixed. This succession of restricted optimizations on $S_i$ (i=1 ... N) is repeated iteratively until a stopping criterion is met. It was previously demonstrated that AO is guaranteed to converge, either to a local or global optimum, for any partitioning of the parameters (see J. C. Bezdek and R. J. Hathaway in "Convergence of Alternating Optimization", Neural, Parallel Sci. Comput., vol. 11, no. 4, pp. 351-368, 2003).

In accordance with an implementation of the second embodiment of the proposed solution, a subset of parameters is created for each core position, i.e., the subset $S_n=d_n=\{x_n, y_n, z_n\}$ corresponds to core $C_n$. During AO, instead of cycling over all subsets, the subset for which the parameters are optimized at each iteration is selected based on the gradients resulting from the current core configuration. As will be detailed hereinbelow, the positioning algorithm associates each target gradient with a core in the configuration. The subset selected is the one corresponding to the core that is associated with the target gradient for which the current angular error $\xi_k$ is the largest. Target gradients for which the resulting gradient orientation has little varied (threshold $\delta_{min}$) during the previous iteration (i.e., due to the last modification to the configuration) are ignored in order to avoid selecting repeatedly the same subsets when some errors $\xi_k$ cannot be decreased further. This subset selection strategy provides focusing the optimization on the parameters that are likely to improve the quality of the core configuration the most at each AO iteration. The AO process stops when the largest angular error is below threshold $\varepsilon_{tol}$. The pseudo-code for this AO algorithm is presented in FIG. 9. The input parameter node is a tree search node structure containing the parameters for the current configuration (as described hereinbelow). Note that the input set of target gradients $\{T_1, T_2, \ldots, T_j\}$, where j≤K, does not necessarily contain the whole set of target gradients defined on the vascular path.

Search Algorithm

Given a set of target gradients, the goal is to find a working configuration (position and size) of cores that will distort the magnetic field $B_0$ such that the required gradients are provided (generated). As mentioned earlier, solving this set of equations is not trivial due to the cumulative contribution of each core to the total gradients, the physical constraints on core positions and because of the possible dipole-dipole interactions that can alter the accuracy of the proposed models. In particular, whenever a modification is made to a core configuration to adjust the resulting gradient at a given target point (e.g., a core is moved, resized or a new core is added), significant variations of the total resulting gradients at the other target points may be induced. Although a core configuration can theoretically be found by optimizing Eq. (30) for a given number of cores, the odds of converging to an unsatisfactory local optimum can be high and can increase with the number of cores. The required number of cores is a priori unknown, as well as their characteristics (for example the size). In accordance with the second embodiment of the proposed solution, combining cores of different radii in a configuration of cores can add flexibility for solving the set of equations and may increase the number of possible solutions. In this regard, it is proposed that a configuration is a valid solution when the target gradients and all other constraints are met. Thus, assuming that target gradients are chosen properly, there may be multiple equivalent solutions for navigating agents in a given vascular network.

In accordance with the second embodiment of the proposed solution, an incremental approach for the positioning algorithm is proposed, where the target gradients defined along the desired vascular path are considered and met (solved for) successively. New cores are progressively added to the configuration in order to meet the following target gradient(s) on the sequence of fluid junctions (path) at each step. This approach enables exploring solutions using different core positions and characteristics (for example size) while progressing on the fluid path. In what follows, the available core characteristics to solve a given problem are referred to as core prototypes.

During the search, every target gradient $\mathcal{T}_k$ is associated with the ferromagnetic core $\mathcal{C}_n$ that was added to provide (meet) this target gradient. When positioning regions of different target gradients intersect, multiple target gradients can be associated with the same core (if this core is positioned in an intersection area). This can serve as a heuristic to orient the search while reducing the number of cores in the configuration. For simplicity, however without limiting the invention, the search algorithm is first described for unitary associations (core to target gradient point) only.

Starting from the first target gradient on path (k=1), cores $\mathcal{C}_k$ are added incrementally for each target gradient. Let $\mathcal{T}_k$ be the next target gradient on path and $G'_k$ be the current total gradient at $p_k$, resulting from the current configuration of cores $\mathcal{C}_1, \mathcal{C}_2, \ldots, \mathcal{C}_{k-1}$. The additional gradient required at $p_k$ to obtain $G_k$ is (when expressed in Cartesian coordinates) given by:

$$G_{k,add} = G_k - G'_k \qquad (34)$$

The new core $\mathcal{C}_k$, selected among the core prototypes, is associated with $_k$ and added at one of the three theoretical possible positions $d_{k,i}$ yielding the required additional gradient, which are calculated using Eq. (29). Two issues may then arise: the position of $\mathcal{C}_k$ may not respect some of the physical constraints in Eq. (32)-(33); and the total gradients previously generated at $p_1, \ldots, p_{k-1}$ may have been altered. To overcome the former issue, a physical constraint check is performed when adding a core and, if a constraint is violated, the restricted optimization of Eq. (30) with respect to $\mathcal{C}_k$ and $_k$ only is performed in order to adjust the position of $\mathcal{C}_k$ to a local optimum satisfying the constraints. Then, to address the latter issue, the AO process described previously is performed by taking into account the target gradients $_1, _2, \ldots, _k$. If the resulting configuration containing the new core is valid (i.e., target gradients $_1, \uparrow_2, \ldots, _k$ are met and all constraints are satisfied), the search continues to the following target gradient $_{k+1}$ on the desired fluid path, if any. Otherwise, a different initial position $d_{k,i}$ of $\mathcal{C}_k$ is tested, or a different core prototype when all three positions have been tried. If no valid configuration is found for $_k$, the search backtracks to $_{k-1}$ and tries a different setting for $\mathcal{C}_{k-1}$.

This search algorithm can be implemented as a tree search, where the root node is initialized with the list of all target gradients (tgList={$_1, _2, \ldots, _k$}) and an empty core configuration. The pseudo-code of the proposed methods to expand and process a search node are presented in FIGS. 10 and 11.

Exploiting Positioning Region Intersections

In the algorithm as presented above the number of cores in the solutions being equal to the number of target gradients may become computationally cumbersome and may prevent, due to the physical constraints, finding valid solutions if many target gradients are defined on the path.

In accordance with the second embodiment of the proposed solution intersections between positioning regions of different target gradients, if any, can be employed to orient the search toward solutions using fewer cores (N<K). If, for example, a positioning region of $_k$ intersect with another from a farther target gradient $_p$ on the path, then the new core to be added can be positioned in the intersection area and associated with both target gradients. This possibility can be added in the search tree as an additional child node for $_k$. Thus, one proposed strategy is to include, in the function DFNChildNodes, a test for the positioning region intersections between $_k$ and $_{k+1}, _{k+2}, \ldots, _K$ once a core prototype is selected. Note that this test must take into account the additional gradients needed at $p_k, p_{k+1}, \ldots, p_K$ according to the current core configuration. The tree search algorithm can then be configured to explore the nodes corresponding to intersections first.

Algorithm Implementation

As an example and without limiting the invention, the multi-core positioning algorithm for multi-core DFN-S was implemented in MATLAB® R2013a. The optimizations of Eq. (30) were performed using the sequential quadratic programming (SQP) solver available using the MATLAB® function fmincon from in the Optimization Toolbox. The parameters used for the AO algorithm are $\varepsilon_{tol} = \delta_{min} = 0.01$ rad and maxIter=10.

Figure 12A:
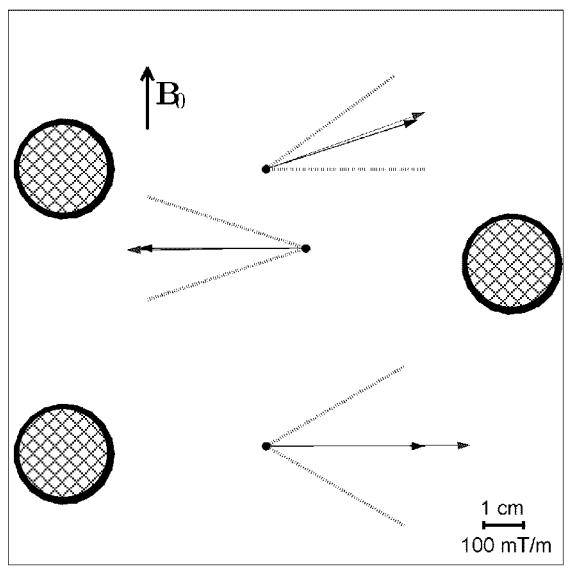
FIGS. 12A, 12B and 12C are schematic diagrams illustrating example solutions of core configurations found by the positioning algorithm of FIGS. 9, 10 and 11 for three different scenarios in 2D in accordance with an implementation of the second embodiment of the proposed solution.
Figure 12B:
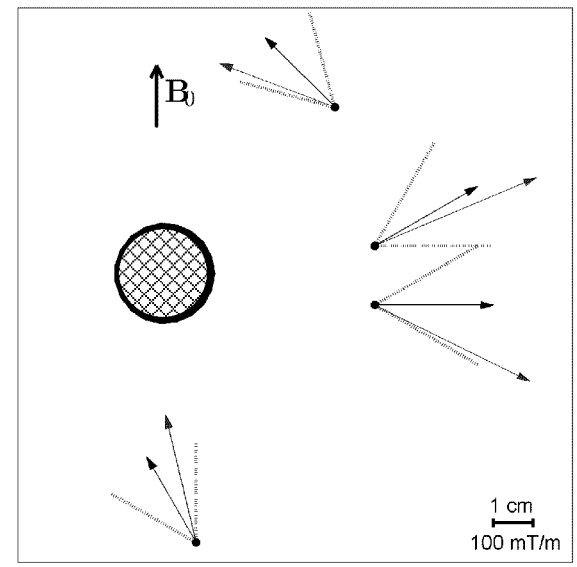
Figure 12C:
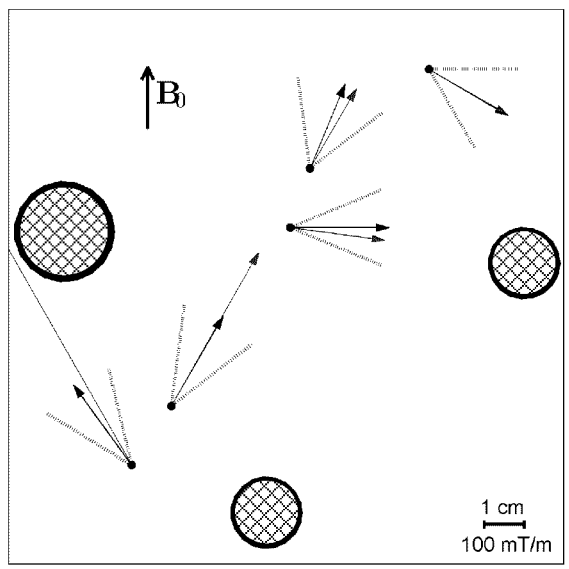

The proposed positioning algorithm was implemented in 2D and 3D. FIG. 12 presents example solutions of core configurations found by the positioning algorithm for three different scenarios, including solutions using positioning region intersections and cores of different radii. The arrows illustrate the desired and resulting gradients. The dotted lines illustrate the angular error tolerance on the gradient orientations. In FIG. 12A, the number of cores is equal to the number of target gradients. In FIGS. 12B and 12C, positioning region intersections are employed to reduce the number of cores used. In FIG. 12C, two core prototypes of different radii were provided to the algorithm. For demonstration purposes only and without limiting the invention thereto, examples are only provided in 2D to simplifying visualization. Equivalent results are obtained in 3D.

Experimental results for the in vitro navigation of magnetic particles through three consecutive junctions (bifurcations) in a 3D vascular network are provided.

In Vitro Multi-Core Navigation Experiment

As a proof of concept, magnetic particles were steered successfully in three consecutive bifurcations in a 3D in vitro network.

An in vitro experiment was conducted in order to evaluate the feasibility of DFN to guide magnetic agents through multiple bifurcations in a vascular network. The experiment consisted in the navigation of magnetic particles in three consecutive bifurcations in a 3D network, using a core configuration found by the algorithm presented hereinabove.

Transparent plastic tubes, having an inner diameter of 1.59 mm, were connected using Y-junctions of equal inner diameter and formed a network with multiple fluid junctions (bifurcations). For each junction, the angle between the two branches (bifurcations) was 60°. The desired path of the particles in the network included three consecutive fluid junctions (bifurcations), with reference to FIG. 13 respectively left, up and then right. The line depicts the desired path of the magnetic particles. These three junctions were glued on LEGO® blocks and the setup was mounted on a baseplate in order to fix their positions in 3D space. The distance between the first and the second bifurcations was ~4.7 cm, whereas the distance between the second and the third was ~3.2 cm.

Figures 13, 14:
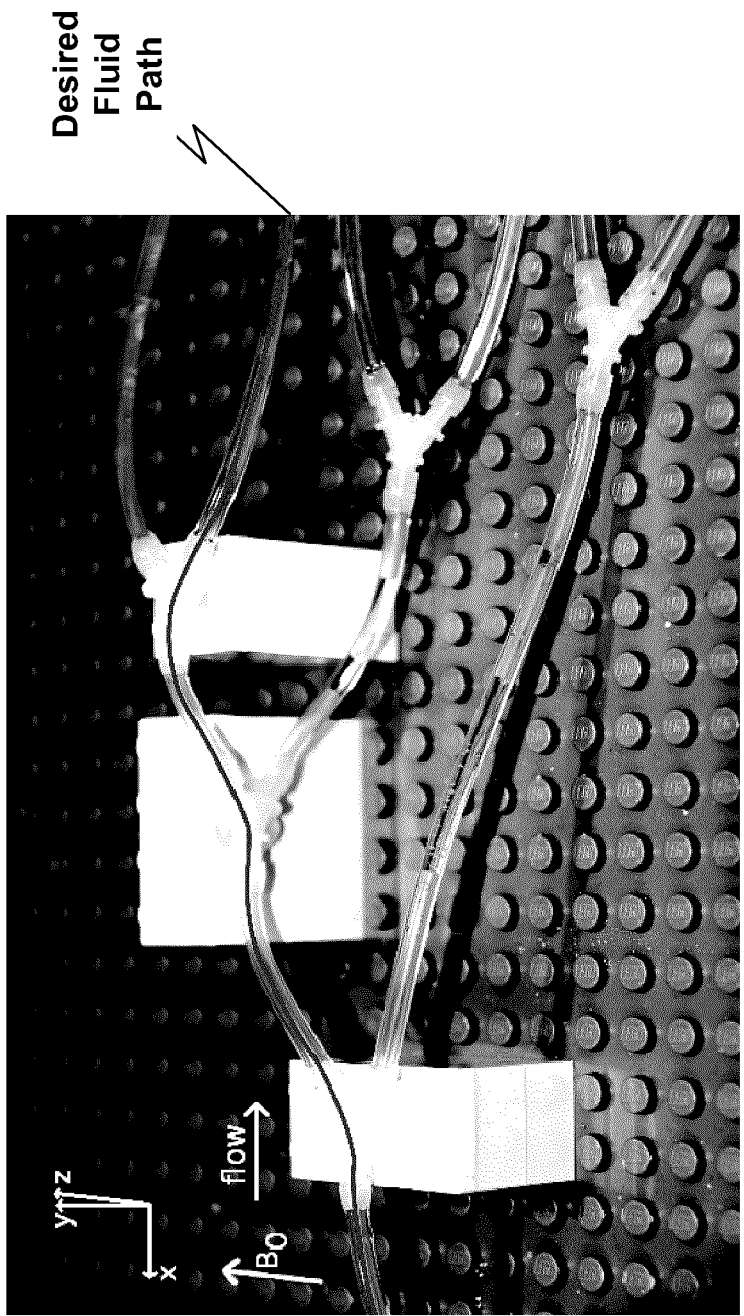
FIG. 13 depicts in perspective view a tube network for a magnetic nanoparticle navigation experiment in accordance with another implementation of the second embodiment of the proposed solution.
FIG. 14 is table showing parameters employed in an experimental setup in accordance with the implementation of the second embodiment of the proposed solution.

The setup was centered in the tunnel of a 1.5 T Siemens Sonata clinical MRI scanner and oriented such that the baseplate lied on the xz-plane and the direction of $B_0=B_0\hat{z}$ was perpendicular to the general direction of the flow, as illustrated in FIG. 13. A target gradient was defined for each junction (bifurcation), with the target points set 5 mm upstream of each of the junctions. This setting was based on the concept of transit time allowed for the particles to shift to the desired side of the tube's centerline before reaching the fluid junction (bifurcation) point (J.-B. Mathieu and S. Martel, "Steering of Aggregating Magnetic Microparticles Using Propulsion Gradients Coils in an MRI Scanner", Magn. Reson. Med., vol. 63, no. 5, pp. 1336-45, May 2010, which is incorporated herein by reference) although the distance of 5 mm was chosen arbitrarily. The required magnetic gradients were oriented perpendicular to the flow and in the direction of the desired deflection (bifurcation). For each target gradient, the following were set $G_{min}=400$ mT/m and $\xi_{max}=\pi/6$.

Figure 15A:
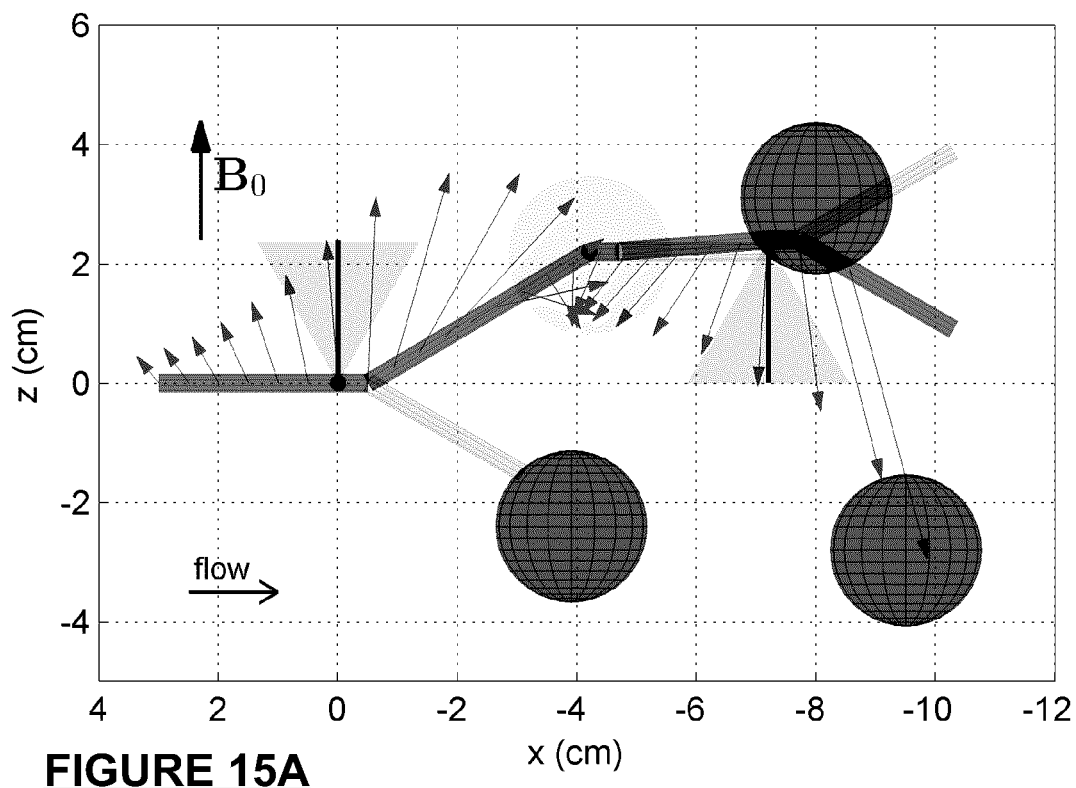
FIGS. 15A and 15B are schematic diagrams respectively illustrating in top view and plan view a core configuration in accordance with the implementation of the second embodiment of the proposed solution.
Figure 15B:
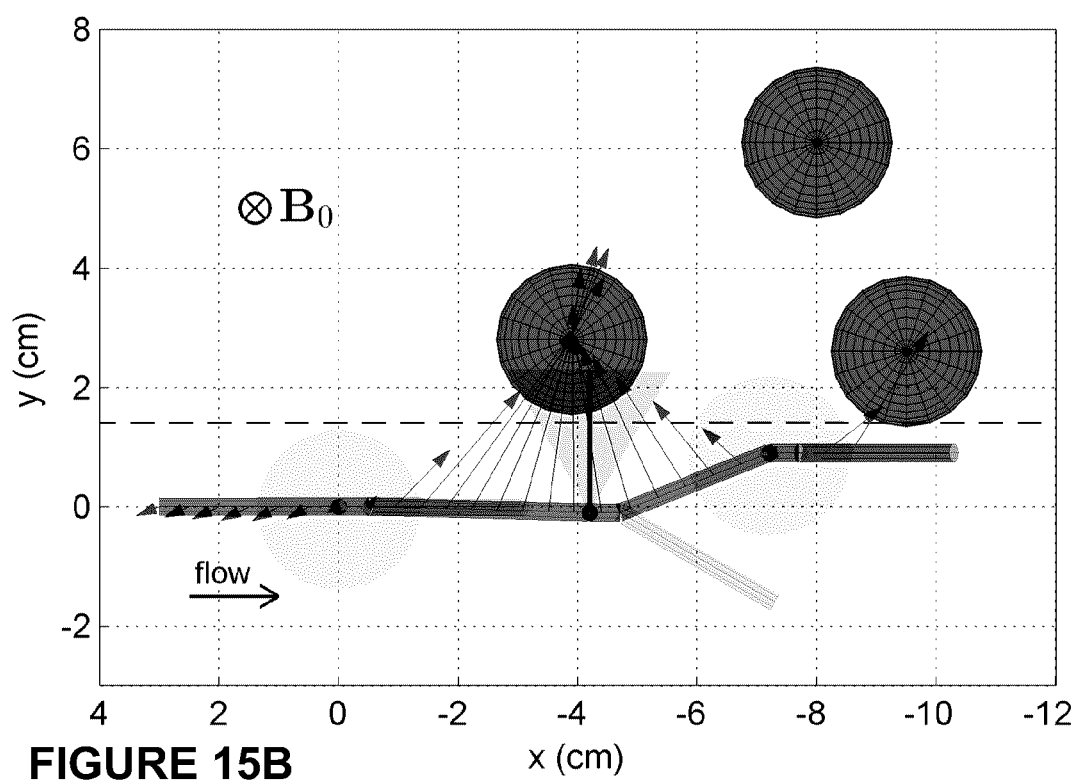

The available ferromagnetic cores for the experiment were carbon steel spherical cores, having a radius R=1.27 cm and a saturation magnetization $M_{sat}=1.43\times10^6$ A/m reached at B≈1.3 T. Thus, the cores were at saturation magnetization inside MRI tunnel. To make the experiment more akin to a real intervention setup, a physical constraint was used in addition to Eqs. (31)-(33) to simulate the presence of a patient's body. As such, the cores were constrained to be located above an imaginary plane (outside the "body" parallel to xz and set 5 mm above the highest target point with respect to the y-axis. The multi-core DFN positioning algorithm presented hereinabove was enabled exploring the whole search tree of this positioning problem. Three different solutions were found, one of which employed only two cores (from the use of positioning region intersections). The other two solutions, including three cores, were nevertheless preferred in order to test multi-core DFN using a more complex core configuration. The solution retained among these two was the one yielding the smallest angular errors on the desired gradients. FIG. 14 presents a table of the various parameters of the experimental setup, including the core positions of the solution used, the resulting gradients at the target points and the angular errors. Note that the first target point was used as the origin of the global xyz-frame. FIGS. 15A and 15B illustrate the core configuration positioned around the tube network and depict the theoretical total resulting gradients along the desired fluid path. The tube network is shown by the heavy lines, with the desired fluid path is illustrated by the darker path. The desired gradients and maximum angular errors are illustrated respectively by the arrows and gray cones. The arrows depict the total gradients along the fluid path, resulting from the positioned cores (spheres). In FIG. 15B, the dashed line represents the (top) limit of the imaginary patient's body. Gradient scale is 6 cm/T.

Figure 16:
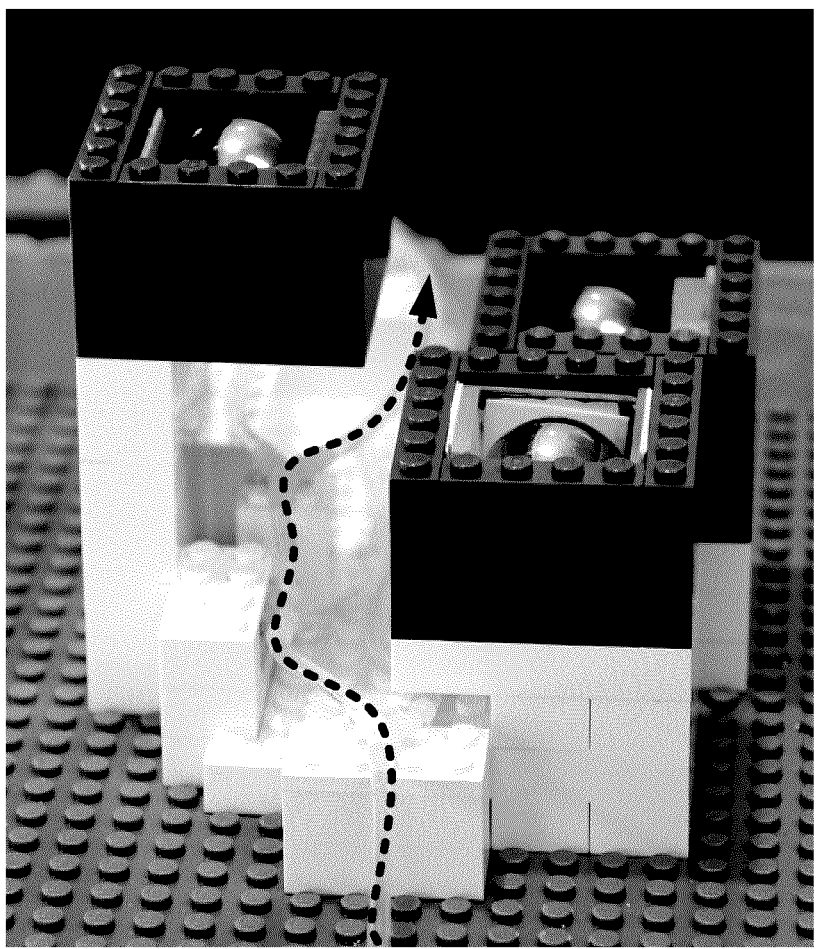
FIG. 16 is illustration showing the experimental setup positioning multiple cores around a tube network in 3D in accordance with the implementation of the second embodiment of the proposed solution.

The cores were added to the setup by placing them in small boxes made of LEGO® blocks and their positions were precisely adjusted using shims as illustrated in FIG. 16. The positioning precision of junctions (bifurcations) and cores in the setup was 1-2 mm.

A blood analogue fluid of dynamic viscosity 3.5 mPa·s consisting of 36% glycerol in water was used as the circulating fluid in the tubes. A syringe pump (Harvard Apparatus PHD 2000) set in refill mode was connected to the outputs of the network such that a constant and equal flow was delivered in both branches for each junction. This ensured that no preferential flow path existed in the network. The flow was set to 20 mL/min before the first junction (bifurcation). This yielded a flow velocity of 16.8, 8.4 and 4.2 cm/s before the first, second and third junctions respectively.

Magnetic particles were fabricated by the microencapsulation of water-based ferrofluid (Ferrotec EMG 700) using sodium alginate. This ferrofluid has a saturation magnetization of 25860 A/m and a density of 1.29 g/cc. The resulting particles varied in diameter between 200-400 μm. These magnetic particles were injected manually before the first junction. An MRI-compatible camera (MRC Systems GmbH, model 12M) was positioned in the tunnel of the MRI scanner in order to record videos of the experiment. Due to their magnetization, the magnetic particles (dark-brown color) formed small aggregates that were easily visible through the tubes in the images.

Results

Figure 17:
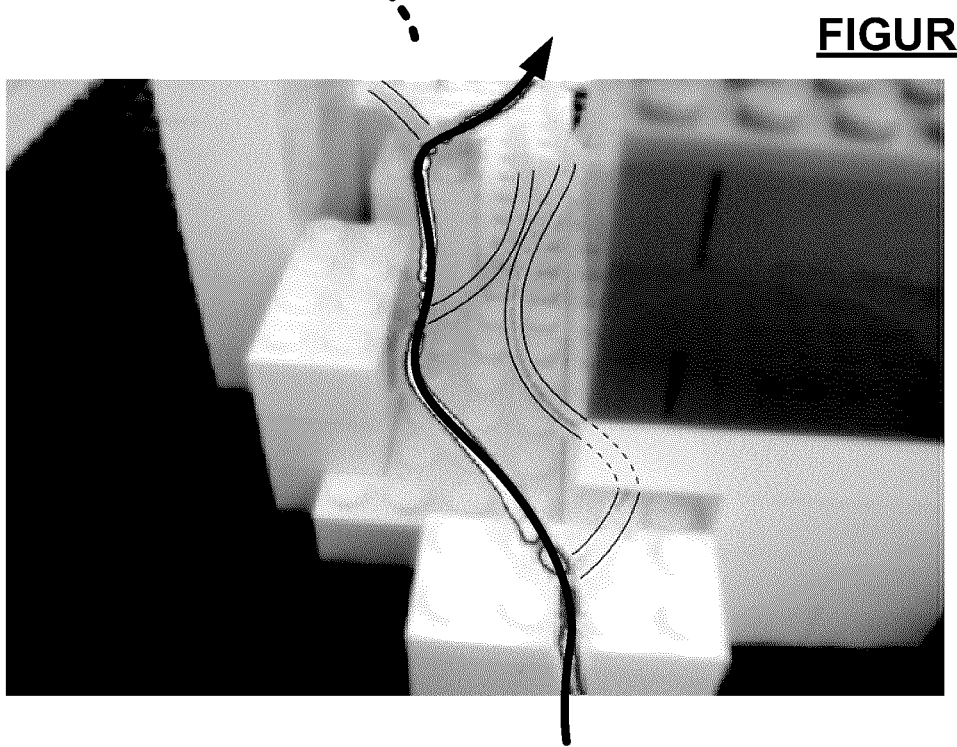
FIG. 17 depicts a 3D density plot overlaid over a perspective view of the experimental setup illustrated in FIG. 16 in accordance with the implementation of the second embodiment of the proposed solution.

Magnetic particles were injected continuously in the network for about 2 min 40 s, while the camera recorded a video of the experiment (30 fps, 640×480 pixels). The video was analyzed by a motion detection algorithm for example implemented in MATLAB. This algorithm performed a frame-by-frame differential analysis in order to detect moving particles or aggregates in the tubes. The distribution of the total motion detected for each pixel was plotted as a "heat map" (density map), superimposed on the average video frame. FIG. 17 illustrates the detected particle motion in the network as a result of this analysis. For simplicity of illustration, the motion density is simplified and shown as a flow path line. Tube locations are emphasized by lines drawn subsequently. Clearly, most of the motion was detected along the desired path, indicating that the majority of particles were steered in the desired junctions (bifurcations). In fact, little motion was detected in the wrong branch of the first junction, and no motion was detected in the wrong branches of the second and the third junctions (bifurcations).

As a more precise evaluation of the navigation efficiency, the steering ratio is defined as the mass fraction of the particles reaching the targeted branch of a junction. In the present case, the steering ratio was estimated by counting the number of particles/aggregates reaching each branch of the three junctions. In order to obtain the most accurate counts as possible, this task was performed manually by analyzing the complete video frame by frame. For the first junction, a total number of 330 particles or aggregates were counted in the left branch, whereas 31 were spotted going through the right branch. This results in an estimated steering ratio of ~91% for the first junction (bifurcation). For both the second and third junctions (bifurcations), where flow velocities were slower, no particles were seen in the wrong branches, thus yielding a steering ratio of 100% in those cases.

Discussion

The navigation experiment conducted demonstrates the potential of multi-core DFN for guiding magnetic particles in a vascular network. An interesting result is that core configurations could be found when the cores were constrained to be positioned above an imaginary patient body. Although the depth of the network inside the "body" was relatively small for this experiment, the depth can be increased using larger cores (M. Latulippe and S. Martel "Dipole Field Navigation for Targeted Drug Delivery", in IEEE Int. Conf. Biomed. Robot. Biomechatronics, 2014, which is incorporated herein by reference).

An issue worth discussing was encountered during the experiment, but does not appear in the results presented. As depicted in FIGS. 15A and 15B, a strong gradient orthogonal to the flow was generated in the targeted branch past the third bifurcation. As the particles reached this region, the particles were trapped inside this high gradient area and could not move farther in the network. While this does not affect the validity of the results presented, this observation highlights the necessity to take into account the magnetic gradients generated throughout the vascular path and not only near the bifurcation points. Such a fluid flow criterion can further improve the method.

As mentioned earlier, it is in theory possible to generate virtually any magnetic path using DFN, provided that the rates of directional changes of the required gradients along the path are limited. The search algorithm presented in this paper is a first attempt at solving the positioning problem for multi-core DFN-S. One current limitation of the specific implementation, however without limiting the invention, relates to the dipole approximation limit constraint, imposing a minimum separating distance between the cores. This constraint restrains the core combination possibilities and probably, but not necessarily, affects the gradient directional change resolution achievable with DFN-S. Further resolution improvements can be obtained under different conditions.

By using larger cores potentially strong magnetic forces may be induced on the cores due to the magnetic interactions. While this was not concern for the core sizes used in the experiment, the forces may reach much higher magnitudes for larger cores. The structure used to retain (maintain) the cores in place should be designed accordingly.

The main possibilities of DFN include depth-independent saturation magnetization of the MNPs, increased strong directional gradients exceeding 300 mT/m in deep tissues, whole-body interventions, reduced peripheral nerve stimulation caused by fast switching gradients and reduced cost of implementation (MRI are already widely available platforms).

The main thrust of the proposed DFN lies in the development of the models and methods for adequately positioning ferromagnetic cores around a patient. The presented algorithm provides solutions for statically positioning multiple cores in order to generate a set of required gradients defined at some points in a vascular network. An implementation algorithm of the proposed method was used to conduct an in vitro experiment, where magnetic particles were successfully guided through three consecutive junctions (bifurcations) in a 3D fluid network. The high targeting levels obtained demonstrate the feasibility and potential of DFN.

The targeted delivery of drugs to tumors in cancer therapy would significantly increase the efficiency of treatments, while minimizing their secondary toxicity for the patients. As such, Dipole Field Navigation is a promising method for navigating untethered magnetic therapeutic agents in a vascular network, method which can provide both the depth-independent saturation magnetization of the agents and high gradient strengths, while being adapted to whole-body interventions.

DFN can be categorized as static or dynamic. For static DFN (DFN-S), the magnetic cores are statically positioned and remain in the same position during the whole intervention as described hereinabove. In DFN-S continuous injections of the microscale agents are possible.

In accordance some embodiments of the proposed solution, to add flexibility to cope with various vascular configurations, dynamic DFN (DFN-D) can be considered where one or more cores are moved during the navigation process for example by using the gradient generated by the MR-imaging coils. In DFN-D, continuous injection may be difficult. For more than one core operating under DFN-D, the cores can be encased in a special assembly with static and/or moving parts allowing independent displacements of a particular core (addressability).

In accordance some embodiments of the proposed solution, a hybrid implementation dubbed "DFN-H" is also possible where statically positioned cores are used with DFN-D. Some examples of the nomenclature used to define the configuration are DFN-S3, DFN-D2, and DFN-H1-2 depicting 3 cores in the static mode, 2 cores in the dynamic mode, and 1 static core with 2 dynamic cores in the hybrid mode respectively. Hereinabove proof of concept has been illustrated for DFN-S3.

In accordance with another embodiment of the proposed solution, for more complex vascular paths with multiple junctions (branch points/bifurcations), several cores would be needed and positioned by considering, and possibly exploiting the magnetic dipole-dipole interactions which may become complex.

Dipole Field Navigation Platforms

One of the applications of Dipole Field Navigation (DFN), as proposed and described herein, is the navigation of magnetic agents in the vascular network (or other body cavities or physiological spaces) for therapeutic, imaging, or diagnostic purposes. Such navigable agents typically contain superparamagnetic nanoparticles acting as Magnetic Resonance Imaging (MRI) contrast enhancement (to assess the position of the agents) and to induce a displacement force via a directional magnetic gradient. Although other types of magnetic nanoparticles could be considered, superparamagnetic nanoparticles are preferred since these have no remnant magnetization once the patient is moved away from the magnetic field. For a given effective quantity or volume of such superparamagnetic nanoparticles embedded in each navigable agent (typically being biodegradable), there are two main variables to be maximized for the induction of a steering or displacement force on such agents. One is the Magnetic Field Strength (MFS) provided by a high magnitude magnetic field B (B is generally defined as the magnetic field density whereas H is generally defined as the magnetic field) and the other is the magnetic gradient G. Unlike permanent magnets, the magnetization of superparamagnetic nanoparticles, such as but not limited to iron-oxide nanoparticles which are used widely as MRI contrast agents, increases with an increase of the MFS until a saturation value is reached known as the saturation magnetization. When at such saturation magnetization, the induction of a displacement force on the nanoparticles would be maximal for a given magnetic gradient. Although employing a non-uniform field are envisioned, and employed in some embodiments of the proposed solution, typically, such a high MFS is provided by a uniform (homogeneous) magnetic field such that no displacement would occur before applying a directional magnetic gradient.

Specialized platform are envisioned and employed in some embodiments of the proposed solution, such MFS is typically provided by taking advantage of the uniform magnetic field $B_0$ typically 1.5 T or 3 T in the tunnel of a clinical MRI scanner. Besides providing a sufficiently high MFS, the same scanner can also be used a priori to gather images of the vascular network before the navigation intervention and to assess the targeting efficacy of the navigable magnetic agents following a navigation phase.

Figure 18:
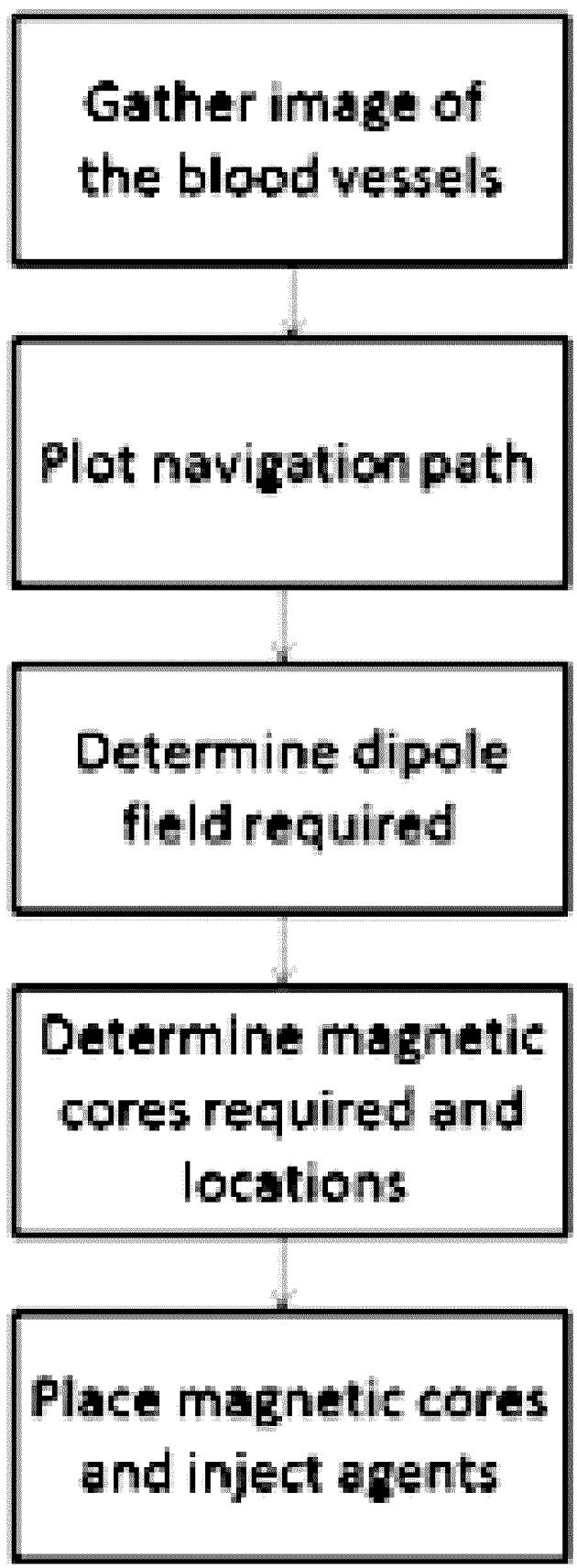
FIG. 18 is a flow diagram showing process steps for placement of magnetic cores in accordance with the proposed solution.

Once such therapeutic agent, for use in some embodiments of the proposed solution, can be magnetized ideally at or near full saturation, directional magnetic gradients can be applied to induce the required displacement forces for navigation purposes along a pre-planned flow path. To increase the gradient beyond what is typically possible with a clinical MRI scanner (for example, as in some embodiments of the proposed solution, by using the imaging gradient coils), and to avoid an overheating of the gradient coils during the navigation phase, DFN employs one or more magnetic cores instead. Such magnetic cores can take various forms (geometries), sizes, and be made of various magnetic materials. Although permanent magnets could be used instead, typically relatively large (typically up to a few centimeters across) spherical soft magnetic cores (e.g., chrome-steel, etc.) are used. When positioned in the magnetic field such as the $B_0$ (H) field of an MRI scanner, such cores typically can reach saturation magnetization, creating a maximum gradient field in the form of a magnetic dipole. Because of this magnetization, each core can distort the field $B_0$ (H) around each core. This distortion in the form of a dipole distortion can correspond to a gradient field, making each magnetic core a source of magnetic gradients. Such cores are then placed at specific locations in the field $B_0$ (H) and around the patient to generate the required set of gradients to force the navigable agents to follow a pre-determined path. In some embodiments of the proposed solution, the distance between neighboring cores can also be made small enough to exploit dipole-dipole interactions (dipolar coupling) to generate the required gradient patterns. A process employed in a typical application is depicted in FIG. 18.

Depending on the implementation of embodiments of the proposed solution, DFN can be categorized as static or dynamic. For static DFN (DFN-S) embodiments of the proposed solution, the magnetic cores are statically positioned and remain in the same position during the whole intervention. Employing DFN-S continuous injection of the navigable agents is possible. To add flexibility to address various vascular configurations, dynamic DFN (DFN-D) embodiments of the proposed solution can be considered where one or more cores can be moved during the navigation process for example, but without limiting the invention, employing gradients generated by the MR-imaging coils of the clinical scanner. For DFN-D, continuous injection may not possible but is not excluded as a possibility.

For DFN-D embodiments of the proposed solution employing more than one core, the cores can be encased in a special assembly referred to herein as a Dipole Field Assembly (DFA). Such DFA can also be employed in DFN-S embodiments of the proposed solution. The DFA can, in the case of DFN-D, include static and/or moving parts allowing independent displacement of a particular core (core addressability). A hybrid implementation of some embodiments of the proposed solution, referred to herein as DFN-H (hybrid) employs statically positioned cores used with DFN-D. Some examples of the nomenclature used herein to define embodiments of the proposed solution, include DFN-S3, DFN-D2 and DFN-H1-2 respectively employing 3 cores in the static mode, 2 cores in the dynamic mode, and three cores 1 static core with 2 dynamic cores in the hybrid mode respectively. Details of DFN-S and DFN-S3 are presented hereinabove.

DFN Platform Configurations

At least some of the DFN platform or system embodiments of the proposed solution, include three components: the field $B_0$ (H) used to increase the saturation value of the magnetic navigable agents, one or more magnetic bodies referred to as magnetic cores being used to distort the field $B_0$ (H) in the form of a magnetic dipole to implement directional magnetic gradients, and a Dipole Field Assembly (DFA) to position one or more of such magnetic cores at the spatial locations within the field $B_0$ (H) and typically outside the patient to deflect (entail) the navigable agents to follow a desired fluid flow trajectory or path. The DFA can be designed to support DFN-S, DFN-D, and DFN-H as described hereinabove. A schematic configuration of a DFN platform is depicted in FIG. 19.

Figure 19:
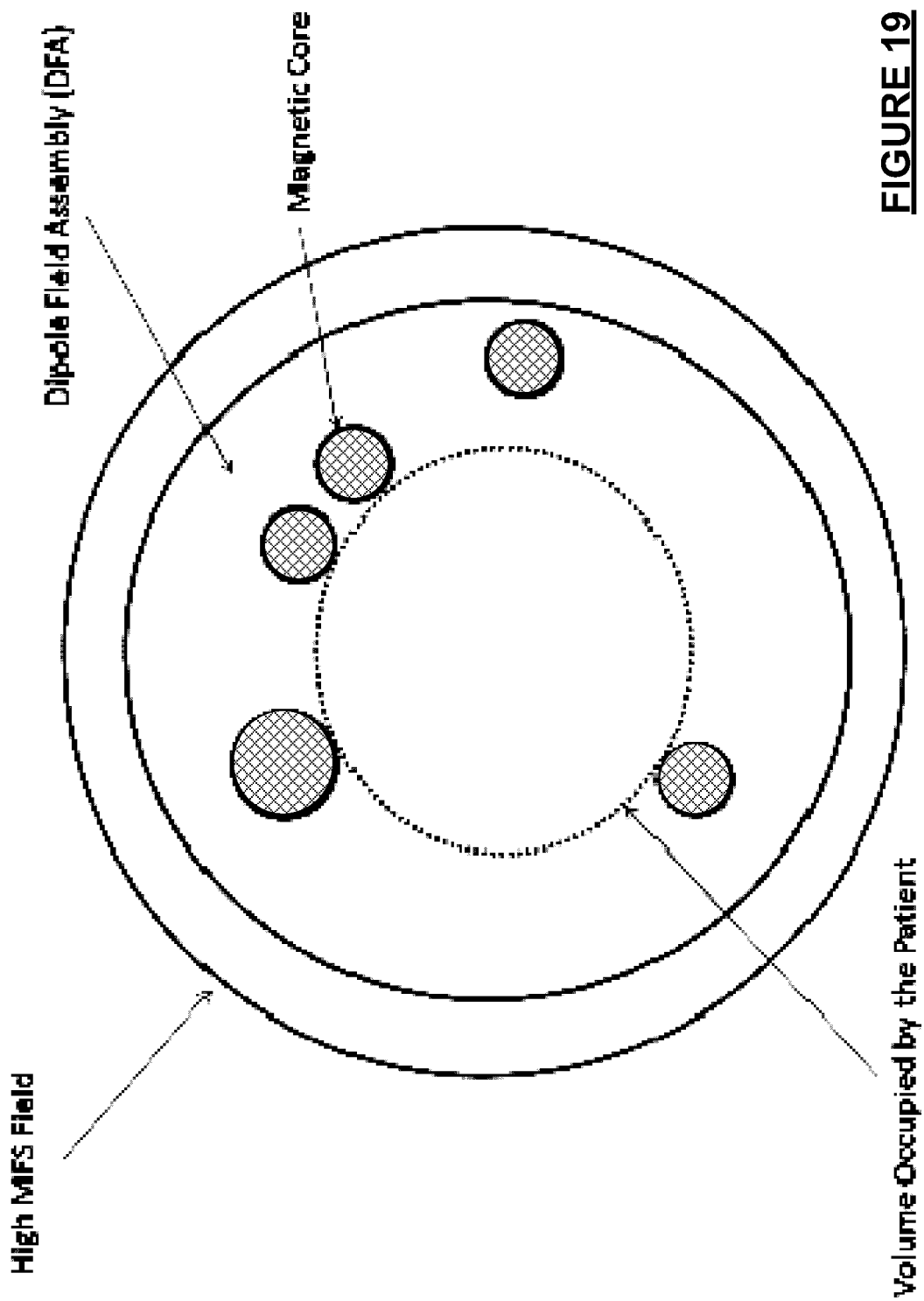
FIG. 19 is a schematic diagram illustrating a configuration of a dipole field navigation platform in accordance with the proposed solution.

In FIG. 19, the high MFS field is sufficiently high at the location of the magnetic cores to produce the required dipole fields that would yield strong enough gradients in the volume occupied by the patient. The DFA in FIG. 19 can take various forms. For DFN-S, the DFA is employed to retain each core at a specific location. The DFA could also allow adjustment of the position of the cores to be made prior to the navigation phase. The DFA could also be removable, in whole or in part, for several reasons such as replacing the DFA by another DFA, or if inside the tunnel of a clinical MRI scanner, to allow MR-imaging to be performed. The displacement of the DFA could be provided manually, or by another mechanism (hydraulic, mechanically, etc.). The gradient field generated by the MR-imaging coils if used inside a clinical MRI scanner can also be employed to move the DFA, for example through the induction of a force to the cores inside the DFA (in some implementations induction of a force to special purpose cores employed for such displacement, for example specially spatially restricted cores).

For DFN-D (including DFN-H), the DFA can provide controlled displacement of the moving cores, each core being moved along a pre-determined trajectory typically outside (and as close as possible if the highest possible gradient for a given core and MFS must be applied) the volume occupied by the patient. The force allowing the displacement of each moveable core can be done by many different mechanism (hydraulic, mechanically, etc.). The gradient field generated by the MR-imaging coils if used inside a clinical MRI scanner can also be used to move cores inside the DFA.

The material used to implement the DFA or part of it could be made flexible to minimize the distance between the cores and the patient. The system could also comprise a library of different DFAs, each differently suited for a particular navigation physiological path or intervention.

Figure 20:
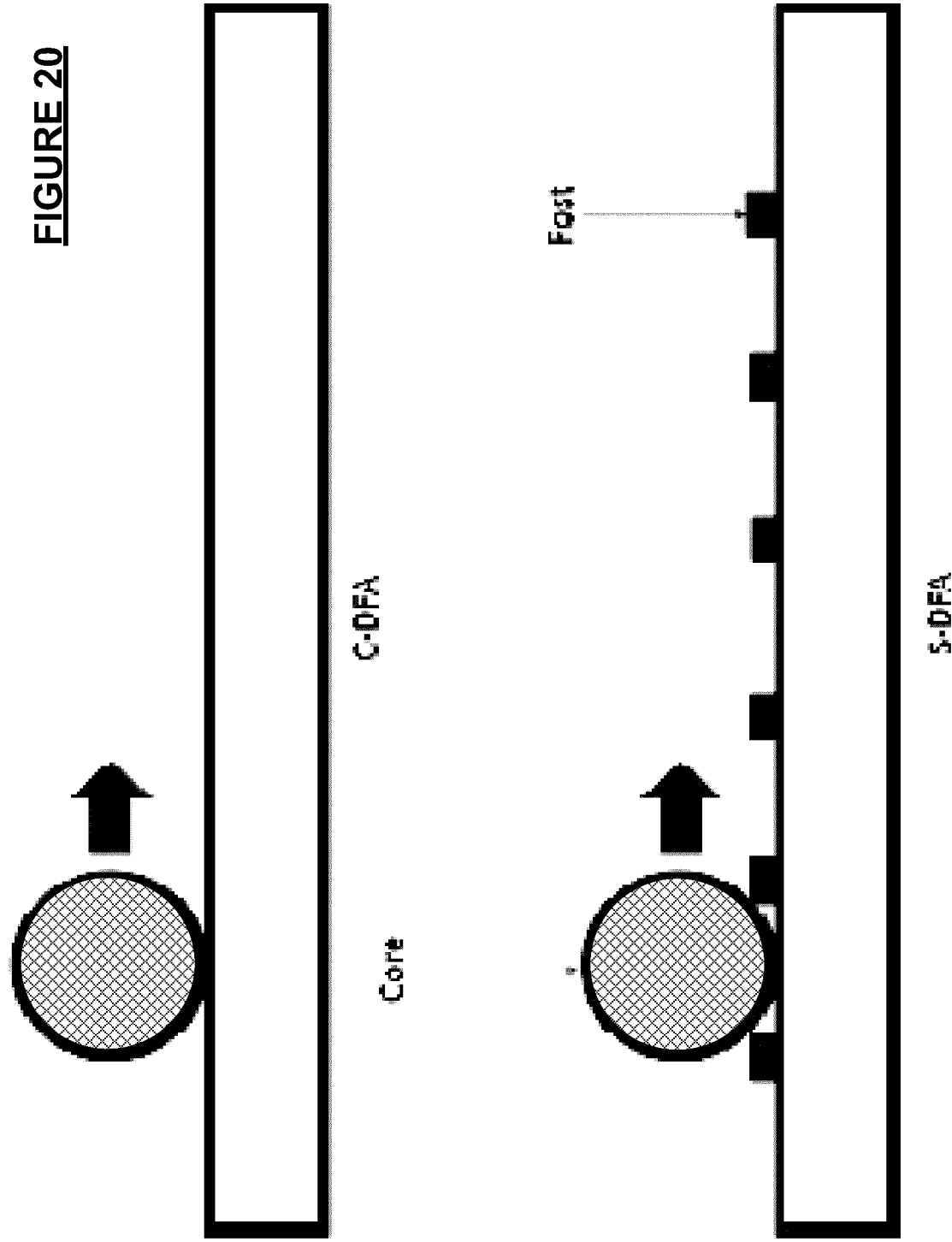
FIG. 20 is a schematic diagram illustrating a configuration of a dipole field assembly in accordance with some embodiments of the proposed solution.

With reference to FIG. 20, in some embodiments of the proposed solution the DFA can be implemented as a stepper-DFA (S-DFA) or continuous-DFA (C-DFA). For S-DFA, the cores can be placed or moved along predefined locations (steps) whereas in a C-DFA, the cores can be free to move for S-DFA, the displacement force can be sufficient for example to pass posts employed to maintain the cores when no displacement force is applied. Such posts could also take various forms. S-DFA can be used for DFN-D as well as for DFN-S.

Figure 21:
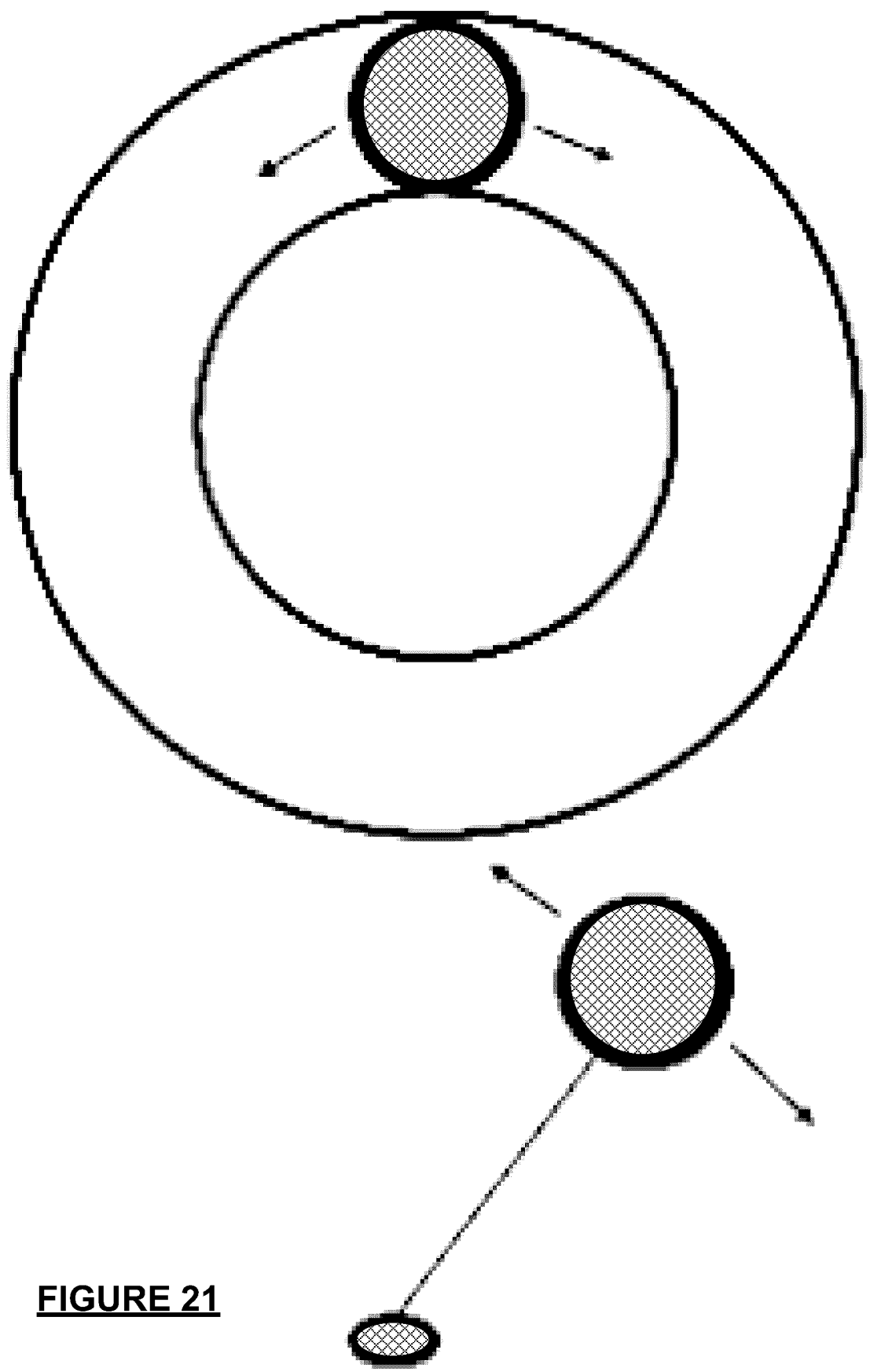
FIG. 21 is a schematic diagram illustrating another configuration of a dipole field assembly in accordance with some embodiments of the proposed solution.

In accordance with some embodiments, the DFA can also have moving parts. Such moving parts could take various forms, such as but not limited to a core encased in a rotary assembly as illustrated in FIG. 21. The core can alternatively be attached to an arm or a similar structure.

For example, in the top section of FIG. 21, the core can be fixed to a rotor. By inducing a force on the core, the rotor can rotate, changing the position of the core along a predetermined trajectory. The same could be achieved by having the DFA fixed and allowing the core to move along the (rotary) channel. Other channel geometries could also be implemented. In the bottom part of FIG. 21, the core can be fixed to a rigid arm that is free to rotate, allowing the core to follow a precise path. Several other configurations are also envisioned. Combining several of these structures with various geometries, angles, etc. can provide specific implementations for embodiments of the proposed solution, including providing DFN-D with several cores.

In other embodiments of the proposed solution, the cores can be in liquid form such as in the form of a ferrofluid. Furthermore, the DFA can provide dispensing and positioning a controlled quantity of such ferrofluid in specific locations where such ferrofluid can be transported in channels and reservoirs through a network of valves.

Figure 22:
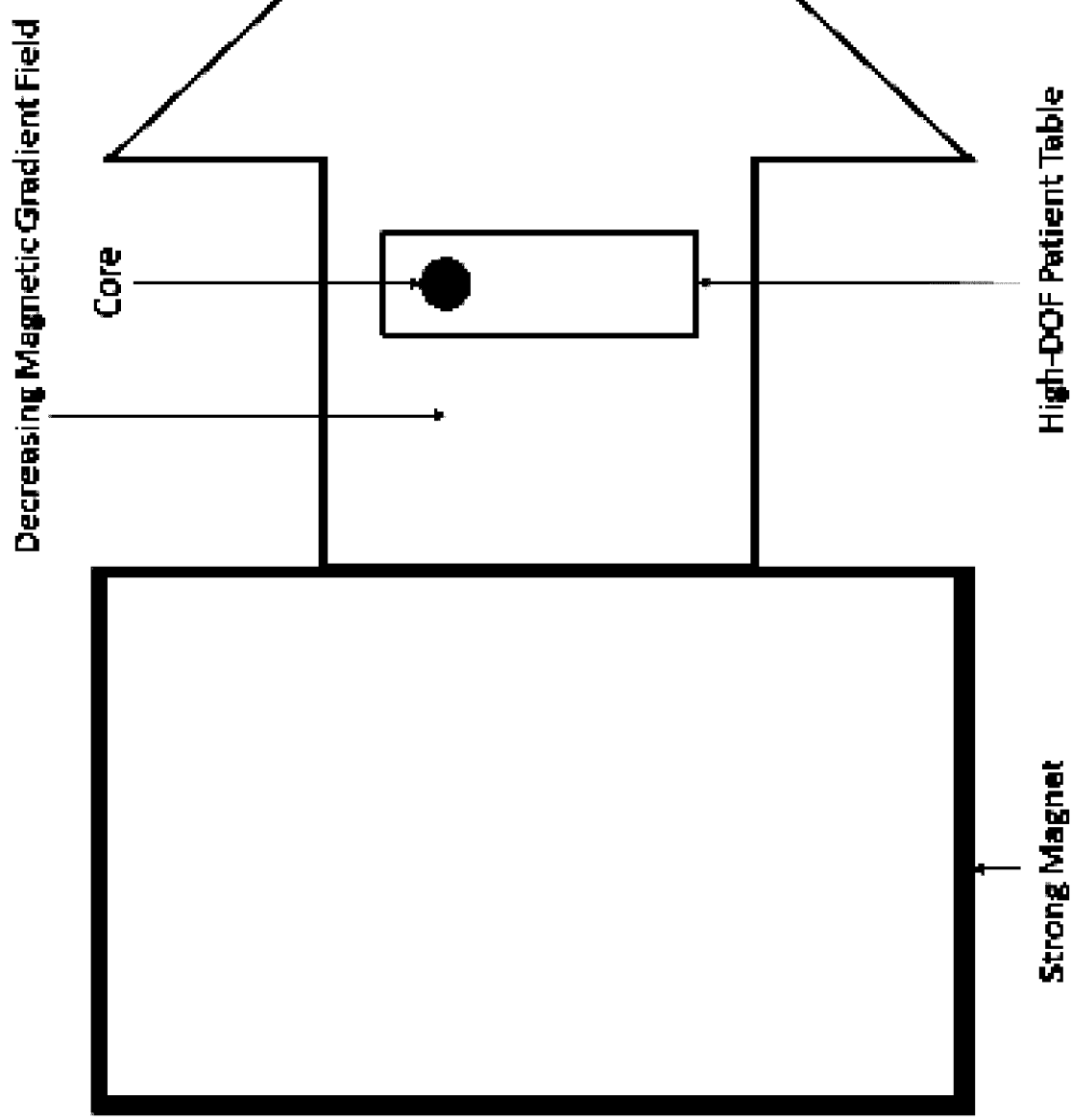
FIG. 22 is a schematic diagram illustrating a further configuration of a dipole field navigation platform configuration in accordance with some embodiments of the proposed solution, wherein similar features bear similar labels throughout the drawings. While the layer sequence described is of significance, reference to "top" and "bottom" qualifiers in the present specification is made solely with reference to the orientation of the drawings as presented in the application and do not imply any absolute spatial orientation.

In accordance with other embodiments of the proposed solution, a further DFN platform configuration is depicted in FIG. 22, wherein the patient is placed on a high degree of freedom (DOF, e.g. 6-DOF) table which is robotically moved in the strong decreasing magnetic field (fringe field) that emanates from a very strong magnet. Such magnet can be the superconducting magnet in a clinical MRI scanner. Such fringe field when the table is close enough to the magnet provides a relatively high MFS and a very high magnetic gradient. By placing a magnetic core of sufficient dimensions, a dipole is created which leads to a gradient that can be used with the high gradient created by the fringe field in order to enhance the performance of the system. Changing the orientation of the gradient can be provided by changing the orientation of the table for example. The core can be fixed or moveable.

For certainty, various process steps are understood to be employed in either in sequence or in parallel without limiting the invention Another drawback is the difficulty of tracking the navigable agents in real-time (for example by imaging) in order to apply corrective actions accordingly during their transit towards the targeted region. This latter issue emphasizes the need for accurate models and the requirement to assess the targeting efficacy on a need basis depending on the expected motion artifacts being encountered during such an intervention.

While the invention has been shown and described with reference to preferred embodiments thereof, it will be recognized by those skilled in the art that various changes in form and detail may be made therein without departing from the spirit and scope of the invention as defined by the appended claims.

What is claimed is:

1. A method for navigating magnetic agents used for therapy, imaging or diagnosis in a vascular network or body cavity of a subject, wherein a body of the subject is to be positioned in a strong magnetic field, the method comprising:

generating a strong and uniform magnetic field with one or more superconducting magnets; and positioning one or more soft magnetic cores on or near the body of the subject for creating magnetic dipole fields within said strong magnetic field, wherein the magnetic dipole fields are able to attract or repel said magnetic agents moving in a blood vessel of said vascular network or said body cavity to navigate towards a target region.

2. The method as defined in claim 1, wherein the magnetic agents comprise therapeutic agents to be navigated across a branch or bifurcation of the blood vessel within the vascular network.

3. The method as defined in claim 1, wherein said one or more superconducting magnets are part of an MRI scanner.

4. The method as defined in claim 1, further comprising providing the magnetic agents for injection into said blood vessel, said magnetic agents being magnetically saturated in said strong magnetic field.

5. The method as defined in claim 1, wherein said one or more soft magnetic cores comprise more than one soft magnetic core, and wherein said one or more soft magnetic cores are positioned for creating a corresponding plurality of dipole fields.

6. The method as defined in claim 1, wherein said positioning comprises calculating suitable positions for said one or more soft magnetic cores.

7. The method as defined in claim 6, wherein said calculating is performed using spatial information about said vascular network or said body cavity of the subject.

8. The method as defined in claim 7, wherein said spatial information is obtained from MRI scan imaging data of an MRI scanner.

9. The method as defined in claim 7, wherein said spatial information is obtained from X-ray, gamma ray or ultrasound imaging data.

10. The method as defined in claim 8, wherein said MRI scanner comprises an MRI tunnel and generates a $B_0$ field that is said strong magnetic field, and further comprising positioning said subject in said MRI tunnel, wherein said positioning of said one or more soft magnetic cores is performed before said positioning said subject in said MRI tunnel.

11. The method as defined in claim 8, wherein said magnetic agents are not guided using steering coils or gradient coils of said MRI scanner.

12. The method as defined in claim 1, wherein said one or more soft magnetic cores is moved during navigation of said magnetic agents.

13. The method as defined in claim 1, wherein said magnetic agents comprise magnetic nanoparticles bound to a non-magnetic agent.

14. The method as defined in claim 13, wherein said magnetic nanoparticles are encapsulated with a non-therapeutic, non-imaging or non-diagnostic agent suitable for binding with said non-magnetic agent.

15. The method as defined in claim 1, wherein said magnetic agents comprise superparamagnetic particles.

16. The method as defined in claim 1, further comprising positioning the subject in an MRI tunnel to provide said strong magnetic field.

17. The method as defined in claim 16, wherein said positioning of said one or more soft magnetic cores is performed after said positioning the subject in the MRI tunnel.

18. The method as defined in claim 1, wherein a force other than a force generated by said strong magnetic field is exerted on at least one of said one or more soft magnetic cores to displace said at least one of said one or more soft magnetic cores during said navigating of said magnetic agents in order to direct said magnetic agents across a plurality of branches or bifurcations of the blood vessels.

19. A method for navigating magnetic agents for therapy, imaging or diagnosis in a vascular network or body cavity of a patient comprising:
   positioning said patient in an MRI tunnel of an MRI scanner, wherein said MRI scanner is configured to generate a strong magnetic field; and
   placing a plurality of soft magnetic cores at different positions on or near a body of said patient while not introducing said plurality of soft magnetic cores into said body of said patient, wherein said plurality of soft magnetic cores are in said MRI tunnel at least when said patient is in said MRI tunnel, for creating magnetic dipole fields within said strong magnetic field, wherein the magnetic dipole fields are adapted to pull or push said magnetic agents moving in a blood vessel of said vascular network or said body cavity of said body of said patient for causing said magnetic agents to navigate towards a target region in said body of said patient.

20. A method for navigating magnetic agents for therapy, imaging or diagnosis in a vascular network or body cavity of a patient comprising:
   generating a uniform strong magnetic field using one or more superconducting magnets, wherein a patient is positioned in said strong magnetic field; and
   placing one or more soft magnetic cores on or near a body of said patient, while not introducing said one or more soft magnetic cores into said body of said patient, for creating magnetic dipole fields within said strong magnetic field, wherein the magnetic dipole fields are adapted to pull or push said magnetic agents moving in a blood vessel of said vascular network or said body cavity of said body of said patient for causing said magnetic agents to navigate towards a target region in said body of said patient.

* * * * *